United States Patent
Rousseau et al.

(12) 
(10) Patent No.: US 11,903,918 B2
(45) Date of Patent: *Feb. 20, 2024

(54) FUMARATE ESTER DOSAGE FORMS WITH ENHANCED GASTROINTESTINAL TOLERABILITY

(71) Applicant: BANNER LIFE SCIENCES LLC, High Point, NC (US)

(72) Inventors: Franck S. F. Rousseau, Chapel Hill, NC (US); Thomas Wallace Lategan, New Orleans, LA (US); Tiffany Nicole Sprague, Greensboro, NC (US); Jason Michael Vaughn, Maineville, OH (US); Justin Roy Hughey, Asheboro, NC (US)

(73) Assignee: BANNER LIFE SCIENCES LLC, High Point, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/143,439

(22) Filed: Jan. 7, 2021

(65) Prior Publication Data

US 2021/0220317 A1  Jul. 22, 2021

Related U.S. Application Data

(60) Provisional application No. 62/959,326, filed on Jan. 10, 2020.

(51) Int. Cl.
*A61K 31/22* (2006.01)
*A61K 9/00* (2006.01)
(Continued)

(52) U.S. Cl.
CPC .......... *A61K 31/22* (2013.01); *A61K 9/0053* (2013.01); *A61K 9/4808* (2013.01);
(Continued)

(58) Field of Classification Search
CPC .. A61K 9/4866; A61K 9/4891; A61K 9/4858; A61K 9/0053; A61K 9/4808;
(Continued)

(56) References Cited

U.S. PATENT DOCUMENTS

| | | |
|---|---|---|
| 5,146,730 A | 9/1992 | Sadek et al. |
| 5,424,332 A | 6/1995 | Speiser et al. |

(Continued)

FOREIGN PATENT DOCUMENTS

| | | |
|---|---|---|
| EP | 0312697 A2 | 4/1989 |
| KR | 100737710 B1 | 7/2007 |

(Continued)

OTHER PUBLICATIONS

Gold et al., "Safety of a novel oral single-agent fumarate, BG00012, in patients with relapsing-remitting multiple sclerosis: results of a phase 2 study," Journal of Neurology 253(Suppl. 2): II144-II145 (2006).

(Continued)

*Primary Examiner* — Savitha M Rao
(74) *Attorney, Agent, or Firm* — Michael Best & Friedrich LLP

(57) ABSTRACT

Described herein are pharmaceutical compositions comprising one or more fumarate esters and methods for treating multiple sclerosis subjects with the compositions where the incidence of gastrointestinal side effects is reduced compared to treatments comprising dimethyl fumarate (e.g., TECFIDERA®). In particular, described herein are oral pharmaceutical compositions comprising monomethyl fumarate in a liquid vehicle that have reduced gastrointestinal side effects.

14 Claims, 5 Drawing Sheets

(51) Int. Cl.
*A61P 1/12* (2006.01)
*A61K 9/48* (2006.01)
*A61P 1/08* (2006.01)

(52) U.S. Cl.
CPC .......... *A61K 9/4825* (2013.01); *A61K 9/4858* (2013.01); *A61K 9/4866* (2013.01); *A61P 1/08* (2018.01); *A61P 1/12* (2018.01)

(58) Field of Classification Search
CPC .. A61K 31/225; A61K 9/4833; A61K 9/4875; A61K 9/10; A61K 45/06; A61K 47/10; A61K 31/485; A61K 47/14; A61K 47/26; A61K 47/42; A61K 9/2013; A61K 9/2018; A61K 9/2031; A61K 9/2063; A61K 9/146; A61K 9/2027; A61K 31/155; A61K 31/22; A61K 31/4196; A61K 31/4725; A61K 31/501; A61K 31/565; A61K 31/662; A61K 9/0019; A61K 9/0073; A61K 9/1635; A61K 9/1652; A61K 9/20; A61K 9/284; A61K 9/2866; A61K 9/2886; A61K 9/4825; A61P 25/28; A61P 1/08; A61P 1/12; A61P 1/16; A61P 15/00; A61P 31/12; A61P 31/14

See application file for complete search history.

(56) References Cited

U.S. PATENT DOCUMENTS

| | | |
|---|---|---|
| 5,459,983 A | 10/1995 | Sadek et al. |
| 6,355,676 B1 | 3/2002 | Joshi et al. |
| 6,436,992 B1 | 8/2002 | Joshi et al. |
| 6,482,516 B1 | 11/2002 | Sadek et al. |
| 6,509,376 B1 | 1/2003 | Joshi et al. |
| 7,157,423 B2 | 1/2007 | Joshi et al. |
| 7,320,999 B2 | 1/2008 | Joshi et al. |
| 7,432,240 B2 | 10/2008 | Joshi et al. |
| 7,612,110 B2 | 11/2009 | Joshi et al. |
| 7,619,001 B2 | 11/2009 | Joshi et al. |
| 7,803,840 B2 | 9/2010 | Joshi et al. |
| 7,915,310 B2 | 3/2011 | Joshi et al. |
| 8,293,270 B2 | 10/2012 | Sukuru |
| 8,333,989 B2 | 12/2012 | Sukuru |
| 8,399,514 B2 | 3/2013 | Lukashev et al. |
| 8,524,773 B2 | 9/2013 | Joshi et al. |
| 8,669,281 B1 | 3/2014 | Zeidan et al. |
| 8,669,282 B2 | 3/2014 | Zicker et al. |
| 8,685,445 B2 | 4/2014 | Hassan et al. |
| 8,759,393 B2 | 6/2014 | Joshi et al. |
| 9,090,558 B2 | 7/2015 | Zeidan et al. |
| 9,302,977 B2 | 4/2016 | Raillard et al. |
| 9,326,947 B1 | 5/2016 | Dyakonov et al. |
| 9,326,965 B2 | 5/2016 | Dyakonov et al. |
| 9,511,043 B2 | 12/2016 | Dyakonov et al. |
| 9,517,209 B2 | 12/2016 | Dyakonov et al. |
| 9,526,965 B2 | 12/2016 | Gatherer |
| 9,566,259 B1 | 2/2017 | Vaughn et al. |
| 9,636,318 B2 | 5/2017 | Vaughn et al. |
| 9,636,319 B1 | 5/2017 | Vaughn et al. |
| 9,814,691 B2 | 11/2017 | Dyakonov et al. |
| 9,814,692 B2 | 11/2017 | Vaughn et al. |
| 9,820,960 B2 | 11/2017 | Dyakonov et al. |
| 9,820,961 B2 | 11/2017 | Vaughn et al. |
| 10,098,863 B2 | 10/2018 | Vaughn et al. |
| 10,105,335 B2 | 10/2018 | Vaughn et al. |
| 10,105,336 B2 | 10/2018 | Dyakonov et al. |
| 10,105,337 B2 | 10/2018 | Dyakonov et al. |
| 10,918,616 B2 | 2/2021 | Dyakonov et al. |
| 10,918,617 B2 | 2/2021 | Dyakonov et al. |
| 10,918,618 B2 | 2/2021 | Scholz et al. |
| 10,945,985 B2 | 3/2021 | Vaughn et al. |
| 2003/0018072 A1 | 1/2003 | Joshi et al. |
| 2004/0054001 A1 | 3/2004 | Joshi et al. |
| 2006/0051345 A1 | 3/2006 | Frohna |
| 2006/0115527 A1 | 6/2006 | Hassan et al. |
| 2006/0165778 A1 | 7/2006 | Hassan et al. |
| 2007/0104778 A1 | 5/2007 | Zeng et al. |
| 2007/0269507 A1 | 11/2007 | Sachetto et al. |
| 2008/0003282 A1 | 1/2008 | Soll et al. |
| 2008/0004344 A1 | 1/2008 | Nilsson et al. |
| 2008/0233185 A1 | 9/2008 | Joshi et al. |
| 2008/0299196 A1 | 12/2008 | Nilsson et al. |
| 2008/0300217 A1 | 12/2008 | Nilsson et al. |
| 2009/0304790 A1 | 12/2009 | Nilsson et al. |
| 2010/0034274 A1 | 2/2010 | Li |
| 2010/0130607 A1 | 5/2010 | Gold |
| 2010/0259906 A1 | 10/2010 | Chang |
| 2010/0278879 A1 | 11/2010 | Manku |
| 2010/0324327 A1 | 12/2010 | Lee |
| 2011/0112196 A1 | 5/2011 | Lukashev |
| 2012/0034274 A1 | 2/2012 | Nilsson et al. |
| 2012/0165404 A1 | 6/2012 | Lukashev |
| 2012/0259012 A1 | 10/2012 | Lukashev |
| 2013/0115281 A1 | 5/2013 | Draper et al. |
| 2013/0216615 A1 | 8/2013 | Goldman |
| 2013/0259906 A1 | 10/2013 | Nilsson et al. |
| 2013/0295169 A1 | 11/2013 | Goldman et al. |
| 2013/0302410 A1 | 11/2013 | Gold |
| 2013/0303613 A1 | 11/2013 | Lukashev |
| 2013/0315993 A1 | 11/2013 | Nilsson et al. |
| 2013/0316003 A1 | 11/2013 | Nilsson et al. |
| 2013/0317103 A1 | 11/2013 | Lukashev |
| 2013/0324539 A1 | 12/2013 | Virsik et al. |
| 2014/0037720 A1 | 2/2014 | Nilsson et al. |
| 2014/0037740 A1 | 2/2014 | Nilsson et al. |
| 2014/0056973 A1 | 2/2014 | Ma et al. |
| 2014/0056978 A1 | 2/2014 | Karaborni et al. |
| 2014/0057917 A1 | 2/2014 | Cundy et al. |
| 2014/0057918 A1 | 2/2014 | Wustrow et al. |
| 2014/0065211 A1 | 3/2014 | Karaborni et al. |
| 2014/0066505 A1 | 3/2014 | Joshi et al. |
| 2014/0099364 A2 | 4/2014 | Nilsson et al. |
| 2014/0163100 A1 | 6/2014 | Dawson et al. |
| 2014/0179779 A1 | 6/2014 | Chao |
| 2014/0193495 A1 | 7/2014 | Nilsson et al. |
| 2014/0199386 A1 | 7/2014 | Nilsson et al. |
| 2014/0199387 A1 | 7/2014 | Nilsson et al. |
| 2014/0199388 A1 | 7/2014 | Nilsson et al. |
| 2014/0199390 A1 | 7/2014 | Nilsson et al. |
| 2014/0199392 A1 | 7/2014 | Nilsson et al. |
| 2014/0199393 A1 | 7/2014 | Nilsson et al. |
| 2014/0200272 A1 | 7/2014 | Nilsson et al. |
| 2014/0200273 A1 | 7/2014 | Nilsson et al. |
| 2014/0200363 A1 | 7/2014 | Guzowski et al. |
| 2014/0205659 A1 | 7/2014 | Nilsson et al. |
| 2014/0275048 A1 | 9/2014 | Zeidan et al. |
| 2014/0275205 A1 | 9/2014 | Zeidan et al. |
| 2014/0275250 A1 | 9/2014 | Cundy et al. |
| 2014/0323570 A1 | 10/2014 | Gold |
| 2014/0348914 A9 | 11/2014 | Karaborni et al. |
| 2014/0348915 A9 | 11/2014 | Karaborni et al. |
| 2014/0350018 A9 | 11/2014 | Cundy et al. |
| 2014/0378542 A1 | 12/2014 | Mao et al. |
| 2015/0024049 A1 | 1/2015 | Nilsson et al. |
| 2015/0079180 A1 | 3/2015 | Karaborni et al. |
| 2015/0132747 A1 | 5/2015 | Lukashev |
| 2015/0190360 A1 | 7/2015 | Cundy |
| 2015/0209318 A1 | 7/2015 | Goldman et al. |
| 2015/0246016 A1 | 9/2015 | Dyakonov et al. |
| 2015/0252013 A1 | 9/2015 | Virsik et al. |
| 2015/0307914 A9 | 10/2015 | Virsik et al. |
| 2015/0366803 A1 | 12/2015 | Lukashev et al. |
| 2016/0101059 A1 | 4/2016 | Dyakonov et al. |
| 2016/0199335 A1 | 7/2016 | Dyakonov et al. |
| 2016/0199336 A1 | 7/2016 | Dyakonov et al. |
| 2016/0237021 A1 | 8/2016 | Bhirud et al. |
| 2017/0056359 A1 | 3/2017 | Vaughn et al. |
| 2017/0056360 A1 | 3/2017 | Vaughn et al. |
| 2017/0071891 A1 | 3/2017 | Dyakonov et al. |
| 2017/0100360 A1 | 4/2017 | Dyakonov et al. |
| 2017/0100361 A1 | 4/2017 | Vaughn et al. |

(56) References Cited

U.S. PATENT DOCUMENTS

| | | |
|---|---|---|
| 2017/0100362 A1 | 4/2017 | Vaughn et al. |
| 2017/0231942 A1 | 8/2017 | Vaughn et al. |
| 2019/0008818 A1 | 1/2019 | Dyakonov et al. |
| 2019/0015372 A1 | 1/2019 | Vaughn et al. |
| 2019/0015373 A1 | 1/2019 | Vaughn et al. |
| 2019/0015374 A1 | 1/2019 | Dyakonov et al. |

FOREIGN PATENT DOCUMENTS

| | | |
|---|---|---|
| WO | 2005023241 A1 | 3/2005 |
| WO | 2006023629 A2 | 3/2006 |
| WO | 2010022177 A2 | 2/2010 |
| WO | 2010079222 A1 | 7/2010 |
| WO | 2012013331 A2 | 2/2012 |
| WO | 2013076216 A1 | 5/2013 |
| WO | 2013090799 A1 | 6/2013 |
| WO | 2013092269 A1 | 6/2013 |
| WO | 2013112859 A1 | 8/2013 |
| WO | 2013148690 A1 | 10/2013 |
| WO | 2013158969 A1 | 10/2013 |
| WO | 2014028299 A1 | 2/2014 |
| WO | 2014190056 A2 | 11/2014 |
| WO | 2015028472 A1 | 3/2015 |
| WO | 2015044853 A2 | 4/2015 |
| WO | 2015086467 A1 | 6/2015 |
| WO | 2015089420 A1 | 6/2015 |
| WO | 2015105757 A1 | 7/2015 |
| WO | 2015128492 A1 | 9/2015 |
| WO | 2016057133 A1 | 4/2016 |
| WO | 2017040272 A1 | 3/2017 |

OTHER PUBLICATIONS

Gullapalli, "Review: Soft Gelatin Capsules (Softgels)", Journal of Pharmaceutical Science, vol. 99, No. 10, 2010, pp. 4107-4148.

Kappos et al., "BG00012, a novel oral fumarate, is effective in patients with relapsing-remitting multiple sclerosis," Multiple Sclerosis 2(Suppl. 1):S85 (2006).

Schilling et al., "Furmaric acid esters are effective in chronic experimental autoimmune encephalomyelitis and suppress macrophage infiltration," Clinical and Experimental Immunology 145(1):101-107 (2006).

Schimrigk et al., "Oral fumaric acid esters for the treatment of active multiple sclerosis: an open-label, baseline-controlled pilot study," European J. Neurology 13(6):604-610 (2006).

Sheikh et al., "Tolerability and pharmacokinetics of delayed-release dimethyl fumarate administered with and without aspirin in healthy volunteers," Clinical Therapeutics 35(10):1582-1594 (2013).

Biogen IDEC, "TECFIDERA, Prescribing Information", Mar. 2013, 21 pages.

Verma, R.K. et al., "Formulation Aspects in the Development of Osmotically Controlled Oral Drug Delivery Systems," Journal of Controlled Release, 79:7-27 (2002).

Yeh et al., "Effect of Medium-Chain Glycerides on Physiological Properties of Rabbit Intestinal Epitheliun1 in Vitro," Pharma. Res. 11(8):1148-1156 (1994).

International Search Report and Written Opinion for Application No. PCT/US21/12418 dated Mar. 25, 2021 (13 pages).

FUMARATE ESTER DOSAGE FORMS WITH ENHANCED GASTROINTESTINAL TOLERABILITY

CROSS-REFERENCE TO RELATED APPLICATION(S)

This application claims priority to U.S. Provisional Patent Application No. 62/959,326, filed on Jan. 10, 2020, the entire contents of which are fully incorporated herein by reference.

TECHNICAL FIELD

Described herein are pharmaceutical compositions comprising one or more fumarate esters and methods for treating multiple sclerosis subjects with the compositions where the incidence of gastrointestinal side effects is reduced compared to treatments comprising dimethyl fumarate (e.g., TECFIDERA®). In particular, described herein are oral pharmaceutical compositions comprising monomethyl fumarate in a liquid vehicle that have reduced gastrointestinal side effects.

BACKGROUND

Fumarate esters, including dialkyl fumarates and monoalkyl fumarates are pharmacologically active organic substances useful for treating hyperproliferative, inflammatory, or autoimmune disorders. Both dimethyl fumarate (DMF) and monomethyl fumarate (MMF) activate the nuclear factor erythroid-derived 2-like (Nrf2) pathway in vitro and in vivo in humans. The Nrf2 pathway is involved in the cellular response to oxidative stress. MMF has also been identified as a nicotinic acid receptor agonist in vitro.

TECFIDERA® (dimethyl fumarate) is indicated for the treatment of patients with relapsing-remitting forms of multiple sclerosis. See TECFIDERA® Prescribing Information, January 2017 at 2 (Biogen Inc.), which is incorporated herein in its entirety for the teachings thereof. TECFIDERA® is formulated as hard gelatin delayed-release capsules containing 120 mg or 240 mg of enterically coated DMF minitablets.

Upon oral ingestion, one methyl moiety of DMF is hydrolysed by esterases to form MMF, the bioactive metabolite. After absorption, MMF is believed to interact with immunocytes in the bloodstream. The primary plasma metabolites of DMF are MMF, fumaric acid, citric acid, and glucose. Monomethyl fumarate is further metabolized in the tricarboxylic acid cycle to carbon dioxide and water.

Fumarate esters produce various undesirable side effects, including flushing, headaches, dizziness, eructation, nausea, vomiting, abdominal or intestinal cramps, and diarrhea. High concentrations of the drug released in the stomach are believed to be responsible for such side effects.

Accordingly, it is desirable to develop oral formulations of fumarate esters that provide enhanced bioavailability and lower doses of fumarate esters as compared to TECFIDERA® and that are equally efficacious for treating multiple sclerosis, psoriasis, or other neurodegenerative, hyperproliferative, inflammatory, or autoimmune disorders with fewer or reduced gastrointestinal side effects.

SUMMARY

One embodiment described herein is a pharmaceutical composition comprising: (a) about 85 mg to about 100 mg of monomethyl fumarate in an immediate releasing single-phase non-aqueous liquid vehicle, wherein administration to a subject provides an effective dosage for the treatment of multiple sclerosis or psoriasis with a lower incidence of gastrointestinal side effects as compared to a 120 mg dose of dimethyl fumarate; or (b) about 170 mg to about 200 mg of monomethyl fumarate in an immediate releasing single-phase non-aqueous liquid vehicle, wherein administration to a subject provides an effective dosage for the treatment of multiple sclerosis or psoriasis with a lower incidence of gastrointestinal side effects as compared to a 240 mg dose of dimethyl fumarate. In one aspect, wherein following administration to a subject, the incidence of a gastrointestinal adverse event of at least moderate severity is at least 5% less frequent than the 120 mg dose of dimethyl fumarate. In another aspect, wherein following administration to a subject, the incidence of vomiting and diarrhea is at least 5% less frequent than the 120 mg dose of dimethyl fumarate. In another aspect, a single unit comprising about 170 mg to about 200 mg of monomethyl fumarate is administered at each dosage. In another aspect, two units comprising about 85 mg to about 100 mg of monomethyl fumarate are contemporaneously administered at each dosage. In another aspect, wherein following administration to a subject, the incidence of a gastrointestinal adverse event of at least moderate severity is at least 5% less frequent than the 240 mg dose of dimethyl fumarate. In another aspect, wherein following administration to a subject, the incidence of vomiting and diarrhea is at least 5% less frequent than the 240 mg dose of dimethyl fumarate. In another aspect, wherein following administration to a subject, on average the subject experiences a Modified Overall Gastrointestinal Symptom Scale (MOGISS) score of ≤4 for GI events earlier in treatment than would occur in treatment with dimethyl fumarate. In another aspect, administration of two units comprising the composition provides more rapid gastric emptying and transit to the subject's duodenum as compared to a single a larger dosage of the monomethyl fumarate. In another aspect, the immediate releasing single-phase non-aqueous liquid vehicle comprises a mixture of mono- and di-glycerides, polyvinylpyrrolidone, polyoxyl 40 hydrogenated castor oil, and lactic acid. In another aspect, the immediate releasing single-phase non-aqueous liquid vehicle comprises: (a) about 30% to about 35% by mass monomethyl fumarate; (b) about 20% to about 50% by mass mono- and di-glycerides; (c) about 0.75% to about 5% by mass polyvinyl pyrrolidone; (d) about 2% to about 12% by mass polyoxyl 40 hydrogenated castor oil; and (e) about 1% to about 5% by mass lactic acid. In another aspect, the composition is encapsulated in an enterically coated soft capsule. In another aspect, the soft capsule comprises a shell comprising: (a) about 20% to about 36% by weight of at least one film-forming polymer; (b) about 8% to about 20% by weight of at least one enteric, acid-insoluble polymer; (c) about 15% to about 20% by weight of at least one plasticizer; (d) about 1% to about 5% by weight of at least one alkali-neutralizing agent; (e) about 20% to about 40% by weight of a solvent; (f) about 1% to about 5% by weight of an opacifying agent; and (g) about 0.05% to about 1% by weight of at least one coloring agent. In another aspect, about 50% of the monomethyl fumarate is released after about 50 min to about 65 min in a pH 6.8 buffer in a USP Apparatus 2 at 37° C. In another aspect, the monomethyl fumarate is consistently released to provide a reduction of gastrointestinal side effects. In another aspect, a nuclear factor (erythroid-derived 2)-like 2 (Nrf2) pathway is activated. In another aspect, the composition is administered orally.

Another embodiment described herein is a pharmaceutical dosage form comprising: (a) about 85 mg to about 100 mg of monomethyl fumarate in an immediate releasing single-phase non-aqueous liquid vehicle, wherein administration to a subject provides an effective dosage for the treatment of multiple sclerosis or psoriasis with a lower incidence of gastrointestinal side effects as compared to a 120 mg dose of dimethyl fumarate; wherein the dosage form has improved bioavailability as compared to 120 mg dimethyl fumarate; or (b) about 170 mg to about 200 mg of monomethyl fumarate in an immediate releasing single-phase non-aqueous liquid vehicle, wherein administration to a subject provides an effective dosage for the treatment of multiple sclerosis or psoriasis with a lower incidence of gastrointestinal side effects as compared to a 240 mg dose of dimethyl fumarate; wherein the dosage form has improved bioavailability as compared to 240 mg dimethyl fumarate. In one aspect, wherein following administration to a subject, the incidence of a gastrointestinal adverse event of at least moderate severity is at least 5% ess frequent than the 120 mg dose of dimethyl fumarate. In another aspect, wherein following administration to a subject, the incidence of vomiting and diarrhea is at least 5% less frequent than the 120 mg dose of dimethyl fumarate. In another aspect, a dosage form comprising about 170 mg to about 200 mg of monomethyl fumarate is administered at each dosage. In another aspect, two dosage forms comprising about 85 mg to about 100 mg of monomethyl fumarate are contemporaneously administered at each dosage. In another aspect, wherein following administration to a subject, the incidence of a gastrointestinal adverse event of at least moderate severity is at least 5% ess frequent than the 240 mg dose of dimethyl fumarate. In another aspect, wherein following administration to a subject, the incidence of vomiting and diarrhea is at least 5% less frequent than the 240 mg dose of dimethyl fumarate. In another aspect, wherein following administration to a subject, on average the subject experiences a Modified Overall Gastrointestinal Symptom Scale (MOGISS) score of ≤4 for GI events earlier in treatment than would occur in treatment with dimethyl umarate. In another aspect, administration of the two dosage forms provides more rapid gastric emptying and transit to the subject's duodenum as compared to a single a larger dosage of the monomethyl fumarate. In another aspect, the immediate releasing single-phase non-aqueous liquid vehicle comprises a mixture of mono- and di-glycerides, polyvinylpyrrolidone, polyoxyl 40 hydrogenated castor oil, and lactic acid. In another aspect, the immediate releasing single-phase non-aqueous liquid vehicle comprises: (a) about 30% to about 35% by mass monomethyl fumarate; (b) about 20% to about 50% by mass mono- and di-glycerides; (c) about 0.75% to about 5% by mass polyvinyl pyrrolidone; (d) about 2% to about 12% by mass polyoxyl 40 hydrogenated castor oil; and (e) about 1% to about 5% by mass lactic acid. In another aspect, the dosage form is encapsulated in an enterically coated soft capsule. In another aspect, the soft capsule comprises a shell comprising: (a) about 20% to about 36% by weight of at least one film-forming polymer; (b) about 8% to about 20% by weight of at least one enteric, acid-insoluble polymer; (c) about 15% to about 20% by weight of at least one plasticizer; (d) about 1% to about 5% by weight of at least one alkali-neutralizing agent; (e) about 20% to about 40% by weight of a solvent; (f) about 1% to about 5% by weight of an opacifying agent; and (g) about 0.05% to about 1% by weight of at least one coloring agent. In another aspect, about 50% of the monomethyl fumarate is released after about 50 min to about 65 min in a pH 6.8 buffer in a USP Apparatus 2 at 37° C. In another aspect, the monomethyl fumarate is consistently released to provide a reduction of gastrointestinal side effects. In another aspect, a nuclear factor (erythroid-derived 2)-like 2 (Nrf2) pathway is activated. In another aspect, the dosage form is administered orally.

Another embodiment described herein is a method for treating or reducing symptoms of multiple sclerosis or psoriasis in a subject comprising administering to a subject in need thereof one or more pharmaceutical dosage forms comprising: (a) about 85 mg to about 100 mg of monomethyl fumarate in an immediate releasing single-phase non-aqueous liquid vehicle, wherein administration to the subject provides an effective dosage for the treatment of multiple sclerosis or psoriasis with a lower incidence of gastrointestinal side effects as compared to a 120 mg dose of dimethyl fumarate; or (b) about 170 mg to about 200 mg of monomethyl fumarate in an immediate releasing single-phase non-aqueous liquid vehicle, wherein administration to the subject provides an effective dosage for the treatment of multiple sclerosis or psoriasis with a lower incidence of gastrointestinal side effects as compared to a 240 mg dose of dimethyl fumarate. In one aspect, a single dosage form comprising about 90 mg to about 100 mg of monomethyl fumarate is administered at each dosage. In another aspect, a single dosage from comprising about 170 mg to about 200 mg of monomethyl fumarate is administered at each dosage. In another aspect, two dosage froms comprising about 85 mg to about 100 mg of monomethyl fumarate is contemporaneously administered at each dosage. In another aspect, the incidence of a gastrointestinal adverse event of at least moderate severity is at least 5% less frequent than the 120 mg dose of dimethyl fumarate. In another aspect, the relative risk reduction (RRR) in the incidence of vomiting and diarrhea is at least 5% less frequent compared with the 120 mg dose of dimethyl fumarate. In another aspect, the incidence Relative Risk of a gastrointestinal adverse event of at least moderate severity is than the 240 mg dose of dimethyl fumarate. In another aspect, the reduction in the relative risk in the incidence of vomiting and diarrhea is at least 5% less frequent than with the 240 mg dose of dimethyl fumarate. In another aspect, on average the subject experiences a Modified Overall Gastrointestinal Symptom Scale (MOGISS) score of ≤4 for GI events earlier in treatment than would occur in treatment with dimethyl fumarate. In another aspect, the dosage form is administered orally. In another aspect, the dosage form is administered after a meal. In another aspect, the meal is a high-fat meal.

BRIEF DESCRIPTION OF THE DRAWINGS

FIG. 2A and FIG. 2B show the same data, with FIG. 2B having the p-value depicted on the graph.

DETAILED DESCRIPTION

Figure 1:
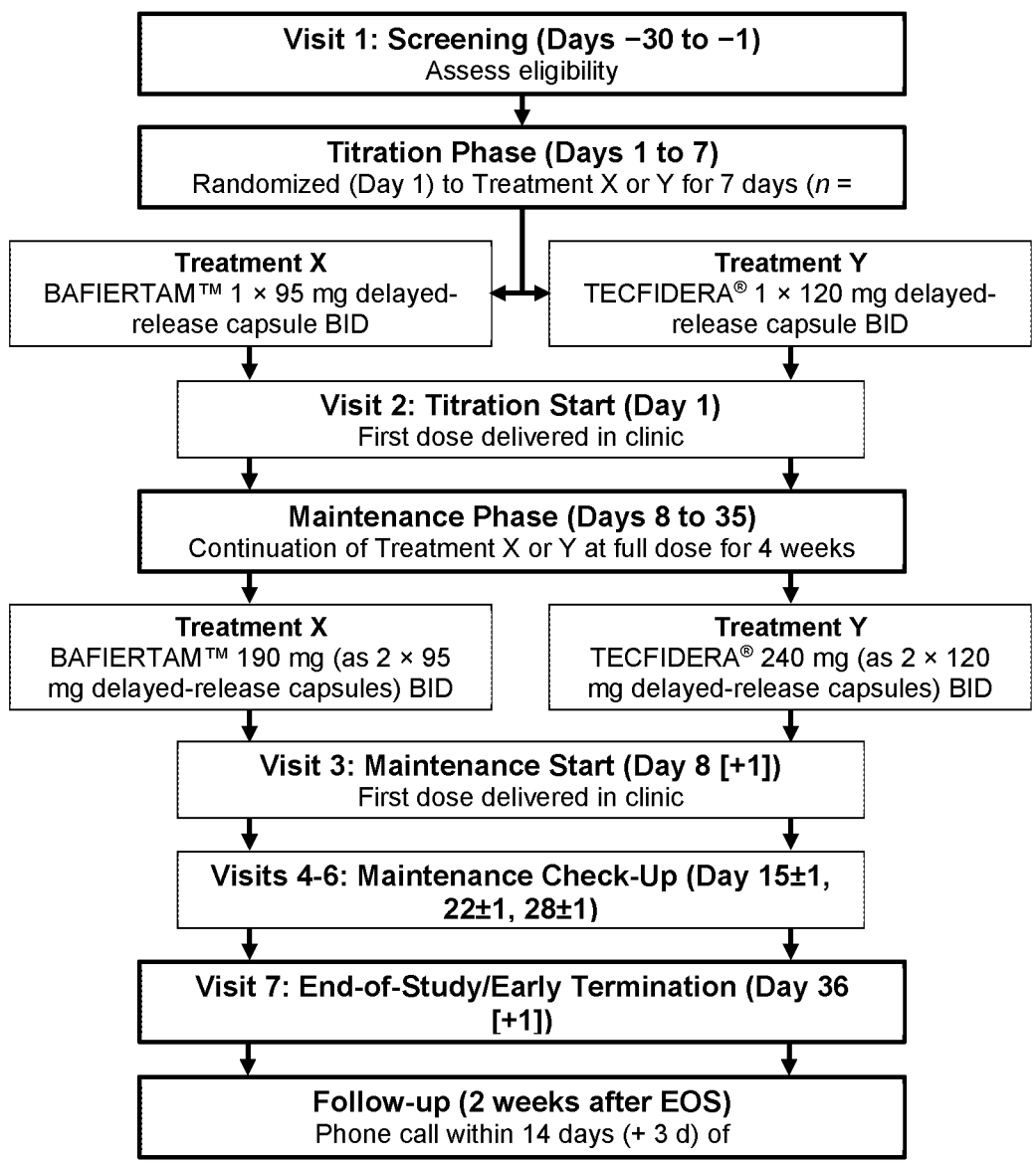
FIG. 1 shows an overview of study design.

Described herein are pharmaceutical compositions of mono- and di-alkyl fumarate esters, such as monomethyl fumarate, pro-drugs of monomethyl fumarate, other pharmacologically active fumarate esters, or combinations thereof.

The pharmaceutical compositions described herein provide one or more fumarate esters or pro-drugs thereof in liquid vehicles. In one embodiment, the composition comprises a single-phase liquid. In another embodiment, the composition comprises a hydrophobic liquid, a hydrophilic liquid, or a combination thereof. In another embodiment, the composition comprises a lipophilic liquid or a lipid liquid. In another embodiment, the composition comprises an aqueous liquid or a hydrophilic, non-aqueous liquid. In another embodiment, the composition comprises a solution of fumarate ester(s), a suspension of fumarate ester(s), or a combination thereof. In one aspect, the composition comprises an emulsion of hydrophilic and hydrophobic vehicles. In one aspect, the composition comprises a fluid, a viscous fluid, a colloid, gel, semisolid, or solid.

In one embodiment described herein, the fumarate ester pharmaceutical composition is a liquid encapsulated within a soft capsule shell. In another embodiment described herein, the fumarate ester pharmaceutical composition is a liquid encapsulated within a hard capsule shell. In another embodiment, the capsule is a soft capsule coated with an enteric coating and one or more subcoatings or top coatings. In another embodiment described herein, the composition is encapsulated in a hard capsule or an enteric hard capsule. In another embodiment described herein, the composition is encapsulated in a hard capsule comprising an enteric coating and one or more subcoatings or top coatings. In another embodiment described herein, the fumarate ester is in the form of a solution or suspension of solid microparticles of defined size in a lipid or lipophilic vehicle. In some aspects described herein, the lipid or lipophilic vehicle may comprise one or more hydrophilic polymers or species, but as described herein, the vehicle is considered a lipid or lipophilic vehicle.

As used herein, the term "fumarate ester" refers to any pharmacologically active mono- or di-alkyl fumarate ester, such as monomethyl fumarate, dimethyl fumarate, or other fumarate esters, acids, salts, pro-drugs of monomethyl fumarate, derivatives thereof, combinations, or mixtures of any of the foregoing. Fumarate ester as used herein also comprises prodrugs that are metabolized to monomethyl fumarate after administration to a subject.

The terms "active ingredient" or "active pharmaceutical ingredient" as used herein refer to a pharmaceutical agent, active ingredient, compound, or substance, compositions, or mixtures thereof, that provide a pharmacological, often beneficial, effect.

The term "dose" as used herein denotes any form of the active ingredient formulation that contains an amount sufficient to produce a therapeutic effect with a single administration.

The term "dosage" as used herein refers to the administering of a specific amount, number, and frequency of doses over a specified period of time, typically 1 day.

The term "dosage form" as used herein refers to any pharmaceutical composition described herein in a form that can be administered to a subject. The dosage form used herein is for oral administration. Exemplary dosage forms described herein include capsules, hard capsules, soft capsules, enteric soft capsules, coated soft capsules, suspensions, solutions emulsions, or the like.

The term "soft capsule" or "soft gel capsule" as used herein refers to a capsule comprising one or more film-forming polymers that is capable of encapsulating a "matrix" or "fill" comprising pharmaceutically acceptable excipients and one or more active pharmaceutical ingredients.

The term "enteric soft capsule" as used herein refers to a soft capsule comprising one or more enteric polymers in the shell or a soft capsule that has been coated with one or more enteric coatings that are applied to the external surface of the capsule as described herein. The coated soft capsule may have one or more subcoatings applied prior to the application of the enteric coating.

The terms "matrix," "fill," or "matrix fill" as used herein refer to a composition comprising one or more active pharmaceutical ingredients that is encapsulated within a capsule. Often the matrix comprises a vehicle, one or more active pharmaceutical ingredients, and one or more pharmaceutically acceptable excipients. In one aspect described herein, the matrix is a liquid and comprises a lipid or lipophilic liquid comprising one or more fumarate esters.

The terms "active pharmaceutical ingredient load" or "drug load" as used herein refers to the quantity (mass) of the active pharmaceutical ingredient comprised in a single soft capsule fill.

The terms "formulation" or "composition" as used herein refers to the drug in combination with pharmaceutically acceptable excipients. This term includes orally administrable formulations as well as formulations administrable by other means.

The term "titration" as used herein refers to the incremental increase in drug dosage to a level that provides the optimal therapeutic effect.

The term "immediate release" as used herein refers to a composition that releases an active ingredient after a short period of time, typically within about 10 to 30 min.

The term "delayed release" as used herein refers to a composition that releases an active ingredient after a period of time, for example minutes or hours, such that the active ingredient is not released initially. A delayed release composition may provide, for example, the release of a drug or active ingredient from a dosage form, after a certain period, under specific physiological conditions, or in a specific condition in an in vitro test. In one aspect as used herein, delayed release refers to the ability of a dosage form to remain intact in the stomach or in vitro at a pH of about 1.2, and then begin releasing the active ingredient in the duodenum or in vitro at a pH of about 6.8 after a short period of time.

The term mean "particle size distribution" (PSD) as used herein refers to the mean particle size from a statistical distribution of a range of particle sizes as described herein. The distribution may be a Gaussian, normal distribution, or a non-normal distribution. The terms such as "d90," "d50," and "d10" refer to the percentage (e.g., 90%, 50%, or 10%, respectively) of particle sizes that are less than a specified size, range, or distribution. For example, "d90≤100 μm" means that 90% of the particle within a distribution are less than or equal to 100 μm.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs and is expressed in units of hours (h) or minutes (min), as applicable.

The term "$AUC_{0 \to \infty}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{overall}$" as used herein refers to the combined area under the blood (plasma, serum, or whole blood) concentration versus time curve, and is expressed in units of h·mg/L (or h·ng/mL) for greater than one dose of the pharmaceutical compositions described herein. In one aspect, the "$AUC_{overall}$" refers to the combined area under the blood concentration versus time curve for at least two doses of the pharmaceutical compositions described herein.

The terms "bioequivalence" or "bioequivalent" as used herein refer to a drug product or dosage form that has highly similar release and systemic absorption as compared to a reference drug. The U.S. Food, Drug and Cosmetic Act (21 U.S.C. § 505(j)(8)(B)(i)) provides that a drug is bioequivalent to a reference listed drug (RLD) if: "the rate and extent of absorption of the drug do not show a significant difference from the rate and extent of absorption of the listed drug when administered at the same molar dose of the therapeutic ingredient under similar experimental conditions in either a single dose or multiple doses."

The phrase "enhanced bioavailability" as used herein refers to the increased proportion of an active pharmaceutical ingredient that enters the systemic circulation when introduced into the body as compared to a reference active pharmaceutical's bioavailability. Bioavailability can be determined by comparing the rate and extent of absorption of a drug with a reference drug when administered at the same molar dose of the active therapeutic ingredient under similar experimental conditions in either a single dose or multiple doses. Typical pharmacokinetic parameters can be used to demonstrate enhanced bioavailability compared to the reference drug.

The term "treating" refers to administering a therapy in an amount, manner, or mode effective (e.g., a therapeutic effect) to improve a condition, symptom, disorder, or parameter associated with a disorder, or a likelihood thereof.

The term "prophylaxis" refers to preventing or reducing the progression of a disorder, either to a statistically significant degree or to a degree detectable to one skilled in the art.

The term "substantially" as used herein means to a great or significant extent, but not completely.

As used herein, all percentages (%) refer to mass (or weight, w/w) percent unless noted otherwise.

The term "about" as used herein refers to any values, including both integers and fractional components that are within a variation of up to ±10% of the value modified by the term "about."

As used herein, "a" or "an" means one or more unless otherwise specified.

Terms such as "include," "including," "contain," "containing," "having," and the like mean "comprising."

The term "or" can be conjunctive or disjunctive.

One embodiment described herein is a pharmaceutical composition comprising one or more fumarate esters for treating multiple sclerosis or other neurological disorders. Particles or micronized powders of one or more fumarate esters can be suspended or solvated in various solutions. The solutions can comprise lipids or lipophilic liquids or aqueous or hydrophilic liquids, or combinations thereof. Such liquids can be encapsulated in capsules, such as hard or soft capsules. In one embodiment, the pharmaceutical composition comprises a non-aqueous, single-phase, flowable liquid. In one embodiment, the pharmaceutical composition comprises a liquid comprising one or more lipid liquids, lipophilic liquids, hydrophilic liquids, or a combination thereof. In one embodiment, the pharmaceutical composition comprises a liquid comprising one or more lipid liquids, lipophilic liquids, or a combination thereof. In one embodiment, the pharmaceutical composition comprises a liquid comprising one or more lipophilic liquids, hydrophilic liquids, or a combination thereof. In one embodiment, the pharmaceutical composition comprises a liquid comprising one or more lipid liquids.

Another embodiment described herein, is an immediate release pharmaceutical composition comprising one or more fumarate esters for treating multiple sclerosis or other neurological disorders. Another embodiment is a delayed release pharmaceutical composition comprising a soft capsule shell encapsulating an immediate release liquid fill comprising one or more fumarate esters. Another embodiment is a delayed release pharmaceutical composition comprising capsule shell coated with one or more subcoatings, one or more enteric coatings, and one or more topcoating moisture barriers encapsulating an immediate release liquid fill comprising one or more fumarate esters. In one aspect, the pharmaceutical composition comprises one or more fumarate esters in an immediate releasing liquid that is encapsulated in an enteric soft capsule that provides delayed release of the fumarate ester in the intestines. In one aspect, the enteric soft capsule is a soft capsule that is coated with one or more enteric polymers. In another aspect, the soft capsule is additionally coated with a moisture barrier that improves the integrity of the capsule and eliminates cosmetic defects such as dimpling, flattening, or capsules sticking to each other.

The fumarate ester particles described herein (e.g., dimethyl fumarate or monomethyl fumarate, or prodrugs of monomethyl fumarate) may be generated by any particle size reduction or particle growth methodology known to one having ordinary skill the art. Exemplary and non-limiting methods comprise "top-down" reductions in particle size including mechanical micronization techniques, where larger particles are comminuted into smaller particles by jet milling, ball milling, or high-pressure homogenization; or particle engineering techniques such as cryogenic spraying or crystal engineering. In addition, "bottom-up" processing may be used to prepare suitable particle sizes as described herein using dual solvent/anti-solvent rapid precipitation techniques. See, *Handbook of Pharmaceutical Granulation Technology*, CRC Press, 3$^{rd}$ Edition, 2010, which is incorporated by reference herein for teachings related to generating pharmaceutical particles. In one aspect described herein, fumarate ester particles of a specified size distribution are produced using milling.

In another embodiment, the pharmaceutical composition comprises liquid fills for fumarate esters, such as dimethyl fumarate, monomethyl fumarate, prodrugs thereof, or derivatives thereof, based on lipids or lipophilic vehicles or hydrophilic vehicles. Some of the described matrices have a hydrophobic (lipophilic) surface in contact with the hydrophilic soft capsule shell to minimize any potential shell-fill interactions, such as when soft capsules are filled with hydrophilic vehicles. In other aspects, the fumarate esters are suspended in non-aqueous hydrophilic solutions containing one or more hydrophilic polymers such as polyvinyl pyrrolidone, polyethylene glycols, propylene glycols, polyoxyl 40 hydrogenated castor oil (e.g., glyceryl polyethylene glycol oxystearate, PEG-40 hydrogenated castor oil; Cremophor® RH 40), or combinations thereof.

Described herein are methods for manufacturing liquid fills comprising fumarate esters, such as dimethyl fumarate, monomethyl fumarate, prodrugs thereof, or derivatives thereof, in a controlled release soft capsule in the form of a suspension, where part or all of the fumarate ester is suspended within the composition. Also provided are compositions and formulations where the fumarate ester is incorporated into a single-phase liquid vehicle.

Also described herein are methods for manufacturing liquid fills comprising fumarate esters or derivatives thereof, in a delayed release soft capsule in the form of a solution and or suspension, where part or all of the fumarate ester is dissolved and/or suspended within the composition.

Another embodiment described herein is a delayed release capsule having a shell and a fill, wherein the fill includes a lipid or lipophilic liquid vehicle comprising a suspension or solution of solid particles of one or more fumarate esters such as dimethyl fumarate, monomethyl fumarate, prodrugs thereof, or derivatives thereof. In another embodiment, the lipid or lipophilic vehicle comprises a liquid lipid or lipophilic vehicle comprising oils, fatty acids, fatty acid esters, or a combination thereof. In one embodiment, the vehicle is a single-phase lipid or lipophilic liquid at room temperature and prevents sublimation of the fumarate ester. In another embodiment, the lipid or lipophilic liquid vehicle comprises one or more oils, mono/diglycerides, polyoxyl hydrogenated castor oils, polyvinylpyrrolidones, or a combination thereof. In another embodiment, the lipid or lipophilic liquid vehicle comprises an oil. In another embodiment, the lipid or lipophilic vehicle comprises mono/diglycerides, polyoxyl hydrogenated castor oils, polyvinylpyrrolidones, or a combination thereof.

Exemplary lipid or lipophilic vehicles comprise mineral oil; light mineral oil; natural oils (e.g., vegetable, corn, canola, sunflower, soybean, olive, coconut, cocoa, peanut, almond, cottonseed, persic, sesame, squalane, castor, cod liver) hydrogenated vegetable oil; partially hydrogenated oils; beeswax; polyethoxylated beeswax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, or stearyl alcohol, inter alia, or combinations thereof. In one embodiment, the liquid comprises solid particles of fumarate ester suspended in a lipid or lipophilic vehicle of vegetable oil, fatty acid, fatty acid ester, or a combination thereof. In one embodiment, the lipid or lipophilic vehicle is a liquid at room temperature (e.g., 25° C.) or physiological temperature (e.g., 37° C.). In one embodiment, the lipid or lipophilic vehicle is soybean oil. In another embodiment, the lipid or lipophilic vehicle comprises medium chain monoglycerides and diglycerides.

In one embodiment, the composition comprises a solvent or solubility enhancing agent. Exemplary solvents or solubility enhancing agents useful for the compositions described herein include Capmul® MCM, Cremophor® RH 40, Captex® 355, Croscarmellose, Crospovidone, Crospovidone CL, Crospovidone CL-F, Crospovidone CL-M, Imwitor® 742, Kollidon® CL, Kollidon® CL-F, Kollidon® CL-M, Labrafac™ Lipophile WL 1349, Labrafil® M2125CS, Labrasol®, Lutrol® F 68, Maisine™ 35-1, mannitol, Miglyol® 812, Pearlitol® Flash, Peceol®, polyethylene glycol 400, polyethylene glycol 600, polyethylene glycol 3350, Plurol® Oleique CC 497, Povidone K 17, Povidone K 30, propylene glycol, or combinations thereof. In one embodiment, the lipid or lipophilic vehicle comprises medium chain mono- and diglycerides (e.g., Capmul® MCM) and polyoxyl 40 hydrogenated castor oil (e.g., macrogolglycerol hydroxystearate; Cremophor® RH 40).

In another embodiment, the composition comprises a one or more hydrophilic solvents or suspension agents. The composition can comprise polyvinylpyrrolidone, polyethylene glycols of molecular weight ranging from about 200 to about 8000 (MN, number average molecular weight), or combinations thereof. In one embodiment, the composition comprises polyvinylpyrrolidone K30 (e.g., Povidone K30). In another embodiment, the composition comprises polyethylene glycol 400 and poly polyvinylpyrrolidone K30.

In another embodiment, the composition comprises a release regulator such as a fatty acid salt, fatty acid ester, or fatty acid polyoxyethylene derivative. The release regulator can also be a surfactant having a hydrophilic/lipophilic balance (HLB) value between about 2 and about 40. The HLB characteristic of surfactants can be determined in accordance with "*Physical Pharmacy: Physical Chemical Principles in the Pharmaceutical Sciences,*" Fourth Edition, pp. 371-373, A. Martin, Ed., Lippincott Williams & Wilkins, Philadelphia (1993), which is incorporated by reference herein for such teachings.

In another embodiment, the composition comprises emulsifying or solubilizing agents such as acacia, cholesterol, diethanolamine, glyceryl monostearate, lanolin alcohols, lecithin, mono- and di-glycerides, monoethanolamines, oleic acids, oleyl alcohols, poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, or combinations thereof.

In another embodiment, the composition comprises a neutralizing agent. Without being bound to any theory, the neutralizing agent it thought to stabilize the fumarate ester in the fill by preventing hydrolysis or ester formation with fatty acids. In one aspect, the neutralizing agent comprises an organic acid, ester, or salt. In another aspect, the neutralizing agent comprises an organic acid. In another aspect, the neutralizing agent comprises one or more of lactate, fumarate, caprylate, caprate, oleate, maleate, succinate, tartrate, citrate, glutamate, gluconate, esters, or salts thereof, or combinations thereof. In one aspect, the neutralizing agent is lactic acid.

In another embodiment, the composition includes a hydrophilic internal phase and a lipid or lipophilic external phase. The hydrophilic internal phase can comprise polypropylene glycol or polyethylene glycol of molecular weight ranging from about 200 to about 8000 ($M_N$, number average molecular weight). In another embodiment, the internal phase comprises hydroalcoholic solutions of cellulose derivatives, polyacrylates, polyvinyl polymers, or combinations thereof. In one embodiment, the internal phase comprises polymers such as methylcellulose, hydroxypropylmethylcellulose, polymethylmethacrylate, or polyvinylpyrrolidone.

In one embodiment, the internal phase of the composition state is "fluid" or "structured." A "fluid" internal phase, as used herein, means a completely flowable liquid whose globules can aggregate to make a larger globule. A "structured" internal phase, as used herein, means a solid, semi-solid, or a gel whose shape is relatively stable and does not usually aggregate to form a large globule. In another embodiment, the external phase comprises a vegetable oil, hydrogenated vegetable oil, fatty acid, fatty acid ester, wax, or a combination thereof. In another embodiment, fumarate ester is dispersed in the internal phase as a solution or suspension.

In one embodiment, the pharmaceutical composition comprises one or more active ingredients comprising one or more fumarate esters. In one embodiment, the pharmaceutical composition comprises a lipid or lipophilic vehicle that provides a solution, suspension, or combination thereof of a fumarate ester. In one embodiment described herein, the fumarate ester is a mono- or di-alkyl fumarate of Formula I:

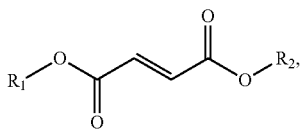

(I)

wherein $R^1$ and $R^2$, which may be the same or different, independently represent hydrogen or a linear, branched, or cyclic, saturated or unsaturated $C_{1-20}$ alkyl radical, which may be optionally substituted with halogen (Cl, F, I, Br), hydroxy, $C_{1-4}$ alkoxy, nitro, or cyano for preparing a pharmaceutical composition as described herein.

The $C_{1-20}$ alkyl radicals, $C_{1-8}$ alkyl radicals, and $C_{4-5}$ alkyl radicals are, for example, methyl, ethyl, n-propyl, isopropyl, n-butyl, sec-butyl, t-butyl, pentyl, cyclopentyl, 2-ethyl hexyl, hexyl, cyclohexyl, heptyl, cycloheptyl, octyl, vinyl, allyl, 2-hydroxyethyl, 2 or 3-hydroxy propyl, 2-methoxy ethyl, methoxy methyl or 2- or 3-methoxy propyl. In one aspect, at least one of $R^1$ or $R^2$ is a $C_{1-5}$ alkyl, especially methyl or ethyl. In another aspect, $R^1$ and $R^2$ are the same or different $C_{1-5}$ alkyl radicals such as methyl, ethyl, n-propyl, or t-butyl. In one aspect, $R^1$ and $R^2$ are the same or different $C_{1-5}$ alkyl radicals such as methyl and ethyl. In one aspect, $R^1$ and $R^2$ are identical and are methyl or ethyl. In one aspect, the fumarate ester is monomethyl fumarate, dimethyl fumarate, methyl ethyl fumarate, or diethyl fumarate. In one aspect, the fumarate ester is monomethyl fumarate, dimethyl fumarate, or a combination thereof. In one aspect, the fumarate ester is monomethyl fumarate. In another aspect, the fumarate ester is dimethyl fumarate.

In one embodiment, the fumarate ester is:

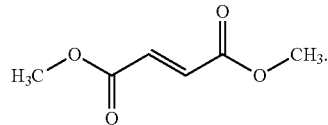

In one embodiment, the fumarate ester is:

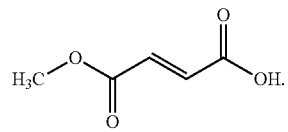

In one embodiment, the fumarate ester is:

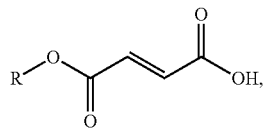

wherein R comprises any $C_{1-20}$ alkyl, any $C_{1-20}$ acid, any $C_{1-20}$ ether, any $C_{1-20}$ ester, any $C_{1-20}$ amino, any $C_{1-20}$ amide, or any $C_{1-20}$ heterocycle.

In another embodiment described herein, the fumarate ester is a prodrug of monomethyl fumarate. In one aspect, the monomethyl fumarate prodrug is dimethyl fumarate. Exemplary monomethyl fumarate prodrugs are described in U.S. Pat. Nos. 8,669,281 and 9,090,558 and U.S. Patent Application Publication Nos. US 2014/0275048; US 2014/0275205; US 2014/0275250; US 2015/0190360; US 2014/057918; US 2014/348914; US 2014/350018; US 2014/056973; US 2014/0348915; and US 2015/0252013, each of which is incorporated by reference herein for such teachings. In one embodiment, the prodrug comprises one or more of N,N-diethylcarbamoyl)methyl methyl(2E)but-2-ene-1,4-dioate; methyl [N-benzylcarbamoyl]methyl (2E)but-2-ene-1,4-dioate; methyl 2-morpholin-4-yl-2-oxoethyl (2E)but-2-ene-1,4-dioate; (N-butylcarbamoyl)methyl methyl(2E)but-2-ene-1,4-dioate; [N-(2-methoxyethyl)carbamoyl]methyl methyl(2E)but-2-ene-1,4-dioate; methyl(N-(1,3,4-thiadiazol-2yl)carbamoyl)methyl(2E)but-2ene-1,4-dioate; (N,N-dimethylcarbamoyl)methylmethyl(2E)but-2-ene-1,4-dioate; (N-methoxy-N-methylcarbamoyl)methyl methyl(2E)but-2-ene-1,4-dioate; bis-(2-methoxyethylamino)carbamoyl]methyl methyl(2E)but-2-ene-1,4-dioate; [N-(methoxycarbonyl)carbamoyl]methyl methyl(2E)but-2ene-1,4-dioate; methyl 2-oxo-2-piperazinylethyl (2E)but-2-ene-1,4-dioate; methyl 2-oxo-2-(2-oxo(1,3-oxazolidin-3yl)ethyl (2E)but-2ene-1,4-dioate; {N-[2-(dimethylamino)ethyl]carbamoyl}methylmethyl(2E)but-2ene-1,4-dioate; ethoxycarbonyloxyethyl methyl (2E)but-2-ene-1,4-dioate; methyl (methylethoxycarbonyloxy)ethyl (2E)but-2-ene-1,4-dioate; (cyclohexyloxycarbonyloxy)ethyl methyl(2E)but-2-ene-1,4-dioate; methyl(2-methylpropanoyloxy)ethyl(2E)but-2-ene-1, 4-dioate; methyl phenylcarbonyloxyethyl (2E)but-2-ene-1, 4-dioate; cyclohexylcarbonyloxybutyl methyl (2E)but-2-ene-1,4-dioate; [(2E)-3-(methoxycarbonyl)prop-2-enoyloxy]ethyl methyl (2E)but-2-ene-1,4-dioate; methyl 2-methyl-1-phenylcarbonyloxypropyl (2E)but-2-ene-1,4-dioate; (cyclohexyloxycarbonyloxy)ethyl methyl (2E)but-2-ene-1,4-dioate; 3-({[(2E)-3-(methoxycarbonyl)prop-2-enoyloxy]methyl}oxycarbonyl)(3S)-3-aminopropanoic acid; 3-({[(2E)-3-(methoxycarbonyl)prop-2-enoyloxy]methyl}oxycarbonyl)(2S)-2-aminopropanoic acid; 3-({[(2E)-3-(methoxycarbonyl)prop-2-enoyloxy]methyl}oxycarbonyl)(3S)-3-(2-aminoacetylamino)propanoic acid; 3-({[(2E)-3-(methoxycarbonyl)prop-2-enoyloxy]methyl}oxycarbonyl)(2S)-2-aminopropanoic acid; 3-{[(2E)-3-(methoxycarbonyl)prop-2enoyloxy]ethoxycarbonyloxy}(2S)-2-aminopropanoic acid; methyl (2-morpholinoethyl)fumarate; methyl (3-morpholinopropyl)fumarate; methyl (4-morpholinobutyl)fumarate; methyl (5-morpholinopentyl)fumarate; methyl (6-morpholinohexyl)fumarate; (E)-2,2'-((2-((4-methoxy-4-oxobut-2-enoyl)oxy)ethyl)azanediyl)diacetic acid; methyl (2-(methyl(2-(methylsulfonyl)ethyl)amino)ethyl)fumarate; 2-(dimethylamino)propylmethylfumarate; (E)-2-((4-methoxy-4-oxobut-2-enoyl)oxy)-N,N,N-trimethylethanaminium; 2-(4,4-difluoropiperidin-1-yl)ethyl methyl fumarate; 1-(dimethylamino)propan-2-yl methyl fumarate; methyl (2-thiomorpholinoethyl)fumarate; methyl (2-(phenylamino)ethyl)fumarate; 2-(dimethylamino)-2-methylpropyl methyl fumarate; methyl (2-(methylsulfonyl)ethyl)fumarate; 2-(1,1-dioxidothiomorpholino)ethyl methyl fumarate; 2-(benzyl(methyl)amino)ethyl methyl fumarate; 2-(2,5-dioxopyrrolidin-1-yl)ethyl methyl fumarate; methyl (2-(piperidin-1-yl)ethyl)fumarate; methyl (2-morpholinoethyl)fumarate; 2-(1,4-dioxa-8-azaspiro[4.5]decan-8-yl)ethyl methyl fumarate; methyl (2-(pyrrolidin-1-yl)ethyl)fumarate; 2-(dimethylamino)ethyl methyl fumarate; 2-(diethylamino)ethyl methyl fumarate; or 2-(diethylamino)-2-oxoethyl methyl fumarate, or pharmaceutically acceptable salts thereof. In one embodiment, the prodrug is (N,N-diethylcarbamoyl)methyl methyl (2E)but-2-ene-1,4-dioate, or a salt thereof. In another embodiment, the prodrug is 2-(2,5-dioxopyrrolidin-1-yl)ethyl methyl fumarate, or a salt thereof.

In one embodiment, the pharmaceutical compositions described herein comprise pharmaceutically acceptable salts of the fumarate ester active pharmaceutical ingredient. The term "pharmaceutically acceptable salts" of an active ingredient includes alkali metal salts such as, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid, inter alia. In another embodiment, the active ingredient may also be in the form of pharmaceutically acceptable uncharged or charged molecules, molecular complexes, solvates, or anhydrates thereof, and, if relevant, single isomers, enantiomers, racemic mixtures, or mixtures thereof. In another embodiment, the active pharmaceutical ingredient may be in any of its crystalline, polymorphous, semi-crystalline, amorphous, or polyamorphous forms, or mixtures thereof.

In another embodiment, the active ingredient comprises a fumarate ester, combined with aspirin, ibuprofen, naproxene, diclofenac, ketoprofen, celecoxib, other non-steroidal anti-inflamatory active drugs (NSAIDs), or combinations thereof.

In one embodiment, the fumarate ester-to-vehicle ratio range (e.g., the ratio of the fumarate ester weight percent to the weight percent of the other components of the fill or vehicle) comprises from about 1:10 to about 1:1 by mass, including all ratios within the specified range. In one aspect, the fumarate ester-to-vehicle ratio comprises about 1:9 to about 1:1 by mass, including all ratios within the specified range. In another aspect, the fumarate ester-to-vehicle ratio range comprises from about 1:5 to about 1:1 by mass, including all ratios within the specified range. In another aspect, the fumarate ester-to-vehicle ratio range comprises from about 1:2 to about 1:1 by mass, including all ratios within the specified range. In one aspect, the fumarate ester-to-vehicle ratio comprises about 1:2.

In one embodiment, the fumarate ester comprises about 5% to about 75% by mass of the composition, including all integers within the specified range. In another embodiment, the fumarate ester comprises about 10% to about 50% by mass of the composition, including all integers within the specified range. In another embodiment, the fumarate ester comprises about 25% to about 50% by mass of the composition, including all integers within the specified range. In another embodiment, the fumarate ester comprises about 70%; about 60%; about 50%; about 40%; about 35%; about 30%; about 25%; about 20%; about 15%; about 10%; about 5%; about 2%; or about 1% by mass of the composition. In one aspect, the fumarate ester comprises about 34% by mass of the composition.

In one embodiment, the pharmaceutical composition comprises about 25% to about 50% by mass of one or more fumarate esters comprising dimethyl fumarate, monomethyl fumarate, or a combination thereof; and about 50% to about 75% by mass of a lipid or lipophilic vehicle. In one aspect, the composition comprises about 34% by mass of one or more fumarate esters. In another aspect, the lipid or lipophilic vehicle comprises about 66% by mass of the composition. In one aspect, the lipid or lipophilic vehicle comprises a mixture of mono- and di-glycerides, polyvinylpyrrolidone, and polyoxyl 40 hydrogenated castor oil. In another aspect, the lipid or lipophilic vehicle comprises a mixture of mono- and di-glycerides, polyvinylpyrrolidone, polyoxyl 40 hydrogenated castor oil, and lactic acid.

In another embodiment, the pharmaceutical composition comprises about 25% to about 50% by mass of one or more fumarate esters, about 40% to about 54% mass of a mixture of mono- and di-glycerides, about 1% to about 10% by mass of polyvinylpyrrolidone, and about 2% to about 10% by mass of polyoxyl 40 hydrogenated castor oil. In one aspect, the composition further comprises and about 1% to about 5% by mass of lactic acid. In one aspect, the fumarate ester comprises dimethyl fumarate, monomethyl fumarate, or a combination thereof.

In another embodiment, the pharmaceutical composition comprises about 20% to about 50% by mass of one or more fumarate esters, about 18% to about 70% by mass of a mixture of mono- and di-glycerides, about 1% to about 10% by mass polyvinylpyrrolidone, and about 2% to about 12% by mass polyoxyl 40 hydrogenated castor oil. In one aspect, the composition further comprises about 1% to about 5% of lactic acid. In one aspect, the fumarate ester comprises dimethyl fumarate, monomethyl fumarate, or a combination thereof.

In another embodiment, the pharmaceutical composition comprises about 34% by mass of one or more fumarate esters, about 48% by mass of a mixture of mono- and di-glycerides, about 3% by mass polyvinylpyrrolidone, and about 10% by mass polyoxyl 40 hydrogenated castor oil. In one aspect, the composition further comprises about 5% by mass of lactic acid. In one aspect, the fumarate ester comprises dimethyl fumarate, monomethyl fumarate, or a combination thereof.

In one embodiment, the solid fumarate ester particles are milled or micronized. In one aspect, the fumarate ester comprises a particle size range of about 10 μm to about 200 μm, including all integers and fractions within the specified range.

In another embodiment, the solid fumarate ester particles have a particle size distribution with d90 of less than or equal to about 200 μm. In one aspect, the solid particles of fumarate ester have a particle size distribution with d90 less than or equal to about 100 μm (d90≤100 μm).

In another embodiment, after solubilization or suspension in the liquid compositions described herein the solid fumarate ester particles have a mean particle size distribution comprising a range of particle sizes with d10≤10 μm. In another embodiment, the solid fumarate ester particles have a mean particle size distribution comprising a range of particle sizes with d50≤30 μm. In another embodiment, the solid fumarate ester particles have a mean particle size distribution comprising a range of particle sizes with d90≤75 μm. In one aspect, after solubilization or suspension in the liquid compositions described herein the fumarate ester particles have particle size distributions with d10≤10 μm, d50≤30, and d90 of ≤75 μm. In another aspect, after solubilization or suspension in the liquid compositions described herein the fumarate ester particles have particle size distributions with d10 of ≤10 μm, d50≤25, and d90 of ≤60 μm.

The forgoing sizes of fumarate ester particles may be determined using standard techniques known to one of ordinary skill in the art. The exemplary techniques that can be used for measuring the size of fumarate ester particles may include laser diffraction analysis, light scattering (e.g., dynamic light scattering), microscopic particle image analysis, elutriation, or aerosol mass spectrometry. The sample of fumarate ester particles may be measured as a dry sample or a wet sample. Any commercially available instrument for measuring particle sizes may be used, including instruments from Cilas; Brookhaven Instruments Corporation; Malvern Instruments; Horiba Scientific; or Wyatt, following the manufacturer's recommended operating procedures.

The measured particle sizes using the techniques described herein may be expressed as a derived diameter with a normal distribution or non-normal distribution with a mean, median (e.g., mass median diameter), and mode of particle diameter sizes. The particle size distribution may be expressed as a diameter number distribution, a surface area distribution, or a particle volume distribution. The mean of the particle size distribution may be calculated and expressed in various ways, such as the volume mean diameter (D[4,3] or $d_{43}$), mean surface area diameter (D[3,2] or $d_{32}$) or the mean number particle diameter (D[1,0] or $d_{10}$). Because the particle size distribution values vary depending on the measurement methodology and how the distribution is expressed, the comparison of different mean particle size distributions must be calculated by the same methodology in order to yield an accurate comparison. For example, a sample with a measured and calculated volume mean diameter must be compared with a second sample having a measured and calculated volume mean diameter, ideally measured using the same measuring instrument under the same conditions. Thus, the specific particle size distributions described herein are not intended to be limited to any one type of method for measuring or calculating a particle size distribution (e.g., a diameter number distribution, a surface area distribution, or a particle volume distribution), but rather indicate particle size values and distributions thereof for each method of measuring particle sizes described herein.

Another embodiment described herein is a method for manufacturing a pharmaceutical composition comprising fumarate ester(s) where the fumarate ester does not sublime during processing, manufacturing, after production, or during storage. Soft capsules comprising fumarate ester in the compositions described herein are stable for months or years. Without being bound to any theory, it is believed that suspending solid fumarate ester particles in a lipid or lipophilic vehicle prevents or retards sublimation and stabilizes the fumarate ester. In one aspect, the pharmaceutical compositions described herein are stable at 25° C. and 60% relative humidity (RH) for about 1 month, about 2 months, about 3 months, about 4 months, about 5 months, about 6 months, about 9 months, about 10 months, about 11 months, about 12 months, about 18 months, about 24 months, or even longer. In another aspect, the pharmaceutical compositions described herein are stable for at least 1 year, or longer at 25° C. and 60% RH. In another aspect, the pharmaceutical compositions are stable for at least 2 years, or longer at 25° C. and 60% RH.

Another embodiment described herein is a method for preparing a pharmaceutical composition comprising a fumarate ester. The method comprises applying heat to the components during mixing or prior to mixing at about the melting point of the composition; and then mixing the fumarate ester with the ingredients using mechanical or ultrasonic forces to form the matrix fill. The composition is flowable such that it can be encapsulated using a rotary die encapsulation machine. In one embodiment, the composition is heated to a temperature in the range of from about 25° C. to about 70° C. In another embodiment, the composition is heated to a temperature in the range of from about 25° C. to about 30° C.

In one embodiment, the composition comprises a lipid or lipophilic vehicle, solid particles of one or more fumarate esters, neutralizing agent, and optional pharmaceutically acceptable excipients. In one aspect, the composition comprises a mixture of mono- and di-glycerides, polyvinylpyrrolidone, polyoxyl 40 hydrogenated castor oil, lactic acid, and solid particles of one or more fumarate esters. In one aspect, the solid particles of one or more fumarate esters are soluble in the composition. In another aspect, the solid particles of one or more fumarate esters are partially soluble in the composition. Without being bound by any theory, it is believed that the solid particles of fumarate ester dissolve or partially dissolve until the solution becomes saturated and the remaining particle exists as a suspension.

In one embodiment, the composition comprises that shown in Table 1 including all possible iterations of the specified ranges that provide 100% total mass percentage.

TABLE 1

Exemplary Composition

| Component | Mass per capsule (mg) | Mass Percent (%) |
| --- | --- | --- |
| Fumarate Ester | 75-220 | 20-50 |
| Vehicle | 300-500 | 50-80 |
| TOTAL | 500-700 mg | 100% |

In one embodiment, the composition comprises about 34% by mass of fumarate ester (d90≤100 μm); about 50% by mass of a mixture of mono- and di-glycerides; about 3% by mass of polyvinylpyrrolidone; about 10% by mass of polyoxyl 40 hydrogenated castor oil, and about 5% by mass of lactic acid.

In one embodiment, the composition comprises one of those shown in Table 2 including all possible iterations of the specified ranges that provide 100% total mass percentage.

TABLE 2

Exemplary Composition

| Component | Mass per capsule (mg) | Mass Percent (%) |
|---|---|---|
| Fumarate ester (d90 ≤ 100 μm) | 80-200 | 30-35 |
| Mono- and di-glycerides | 125-315 | 20-50 |
| Polyvinyl pyrrolidone | 5-32 | 0.75-5 |
| Polyoxyl 40 hydrogenated castor oil | 12.5-75 | 2-12 |
| Lactic acid | 0-32 | 0-5 |
| TOTAL | 625 mg | 100% |

In one embodiment, the pharmaceutical composition comprises a capsule dosage form. In one embodiment, the pharmaceutical composition comprises a soft capsule encapsulating a matrix fill comprising a liquid lipid or lipophilic fill comprising one or more fumarate esters.

In one embodiment described herein, the soft capsule shell has the exemplary composition shown in Table 3.

TABLE 3

Exemplary Soft Capsule Shell Composition

| Component | Mass Percent (%) |
|---|---|
| Film forming polymer (e.g., gelatin) | 20-50 |
| Plasticizer (e.g., glycerol, sorbitol, combinations thereof) | 15-30 |
| Solvent (e.g., water) | q.s. (e.g., 20-40%) |
| TOTAL | 100% |
| Final pH | ~4-7 |
| Ratio total plasticizer to gelatin | 20:43 (0.46:1) |
| Water content in dried soft capsule shell: | 8-15% |

In one embodiment, the soft capsule comprises about 42% of gelatin; about 24% of at least one plasticizer; and about 34% water.

In another embodiment, the soft capsule shell has the exemplary composition shown in Table 4.

TABLE 4

Exemplary Soft Gel Capsule Shell Composition

| Component | Mass Percent (%) |
|---|---|
| Gelatin, 195 Bloom, Lime Bone | 42 |
| Sorbitol (e.g., Polysorb ® 85/70/00; Roquette) | 24 |
| Water | 34 |
| TOTAL | 100% |

Another embodiment described herein includes a process of manufacturing soft capsules comprising any of the pharmaceutical composition as described herein. The process includes preparing a gel mass composition comprising a film-forming, water-soluble polymer, an appropriate plasticizer, and solvent; casting the gel mass into films or ribbons using heat-controlled drums or surfaces; and manufacturing a soft capsule comprising a matrix fill using rotary die technology. The thickness of the films or ribbons that form the soft capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm). In another embodiment, the shell thickness is about 0.035 inches (≈0.889 mm). In another embodiment, the shell thickness is about 0.038 inches (≈0.965 mm). In another embodiment, the shell thickness is about 0.040 inches (≈1.02 mm).

In one embodiment described herein, the soft capsule shell described herein, encapsulates a matrix fill as described herein. In another embodiment described herein, the soft capsule shell and encapsulated matrix fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated matrix fill comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1st Edition, 2013, which is incorporated by reference herein for such teachings.

In one embodiment described herein, soft capsules are coated with an enteric coating comprising the exemplary composition shown in Table 5.

TABLE 5

Exemplary Enteric Coating Composition

| Component | Exemplary Component | Mass Percent (%) |
|---|---|---|
| Enteric Polymer(s) | Methacrylic acid copolymers, polyvinyl acetate phthalates, polyvinyl phthalate, cellulose acetate phthalates, cellulose acetate trimellitate, cellulose acetate succinate, hydroxypropyl methylcellulose, carboxymethyl cellulose | 5-90 |

TABLE 5-continued

Exemplary Enteric Coating Composition

| Component | Exemplary Component | Mass Percent (%) |
|---|---|---|
| Plasticizer(s) | Triethyl citrate, tributyl citrate, polyethylene glycols, propylene glycol, triacetin, dibutyl phthalate, tripropionin, ethyl acid phtalate, butyl acid phthalate, ethyl acid adipate, fats and waxes mixed with esters, glycerin | 0-25 |
| Neutralizing agent | Ammonia, NaOH, sodium bicarbonate | 0-5 |
| Solubilizers | Sodium lauryl sulfate, sodium lauroyl sarcosinate sodium dodecyl sulfate, polysorbate 20, polysorbate 80, other detergents and surfactants | |
| Solvent(s) | Water, ethanol, isopropanol, acetone | 50-80 |
| Excipients | Emulsifiers, pore-forming agents, anti-adherents, surfactants, pigments, colorants, antifoam, antioxidants, waxes, magnesium stearate, micronized amorphous silica, kaolin, talc, | 0-20 |
| TOTAL | | 100% |

Enteric polymers useful for enteric coatings include pH-dependent polymers that are less soluble in an aqueous media with acidic pH and more soluble in an aqueous media with basic pH. In one embodiment, the enteric of pH dependent material dissolves or rapidly disperses at a pH level above pH 5.0, above pH 5.5, or above pH 6.0.

Exemplary enteric polymers useful for coats include cellulose acetate phthalate, hydroxypropylmethyl cellulose phthalate, hydroxypropyl methylcellulose acetate succinate, polyvinyl acetate phthalate, cellulose acetate trimellitate, carboxymethylcellulose, methacrylic acid copolymers such as, Eudragit L (polymethacrylic acid, methylmethacrylate, 1:1 ratio), or Eudragit S (polymethacrylic acid, methylmethacrylate, 1:2 ratio), shellac, zein, or combinations thereof.

Suitable plasticizers include acetyl triethyl citrate, dibutyl phthalate, tributyl citrate, triethyl citrate, acetyl tributyl citrate, propylene glycol, triacetin, polyethylene glycol, diethyl phthalate, or combinations thereof.

Suitable solubilizers include sodium lauryl sulfate, sodium lauryl sarcosinate, sodium dodecyl sulfate, polysorbate 20, polysorbate 80, octylphenoxy polyethoxyethanol, or combinations thereof.

Anti-adherent agents serve to prevent potential agglomeration in acid media. Suitable anti-adherents include talc, magnesium stearate, calcium stearate, stearic acid, hydrogenated vegetable oils, polyethylene glycols, fumed silica, silicon dioxide, or combinations thereof.

Pore-forming agents serve to create pores or channels in the enteric coating after administration to a human. Suitable pore-forming agents include sodium chloride, potassium chloride, sucrose, sorbitol, mannitol, polyethylene glycols (PEG), propylene glycol, hydroxypropyl cellulose, hydroxypropyl methylcellulose, polyvinyl alcohols, methacrylic acid copolymers, poloxamers, or combinations thereof.

Many conventional coating excipients are described in the art. See e.g., Rowe et al., Eds. *Handbook of Pharmaceutical Excipients*, 7$^{th}$ ed. Royal Pharmaceutical Society, UK (2012).

In one embodiment described herein, the enteric coating comprises methacrylic acid and ethyl acrylate copolymer (e.g., EUDRAGIT® L100-55, Evonik), talc, triethyl citrate, sodium bicarbonate, colloidal silica, sodium lauryl sulfate, and water.

In one embodiment, adjusting the amount of enteric coating and the ratio of polymer to other components allows for tuning the release profile of the dosage form.

Subcoats can be applied to the soft capsules prior to coating to prevent shell-coat interactions and improve coating adhesion to the capsule. Exemplary subcoatings can comprise polyvinylpyrrolidone, polyvinyl alcohols, hydroxypropyl methylcellulose, polyethylene glycol, oils, or combinations thereof.

Coatings, top coatings, or subcoatings are applied to the soft capsules using various methods know in the art. The coatings are typically prepared as suspensions and sprayed on capsules in perforated coating pans through one or more spray nozzles at a specific temperature. Coating solutions or dispersion may be applied at spray rates between 100 and 400 g/min. The spray rate may be proportionately higher for coatings with higher solids content and lower for more dilute dispersions. In one embodiment, capsules are coated using a pan coater. After the enteric coating suspension is applied, the coated capsules are dried in the pan coater for a period of time at a specific temperature.

Another embodiment described herein comprises a subcoating that is applied prior to applying an enteric coating. In one embodiment, the subcoating comprises hydroxypropyl methylcellulose, methylcellulose, ethylcellulose, or a combination thereof. In one aspect, the subcoating comprises hydroxypropyl methylcellulose.

Another embodiment described herein comprises a moisture barrier that is applied as a top coating on the enteric coating. In one embodiment, the moisture barrier comprises one or more polyvinyl alcohols and appropriate pharmaceutically acceptable excipients. In another embodiment, the moisture barrier comprises polyvinyl alcohol, sodium lauryl sulfate, glyceryl mono-caprylate-caprate, and talc. In one aspect, the moisture barrier aids in preserving the cosmetic appearance of the dosage forms by preventing dimpling, sticking, or other processing- or storage-induced blemishes.

Another embodiment described herein, is a pharmaceutical composition comprising a matrix fill formulation comprising any of the formulations shown in the Tables or Examples described herein. Any of the components in the formulations described herein, shown in the Tables, or illustrated in the Examples can be increased, decreased, combined, substituted, or omitted to provide for a formulation comprising about 100% by mass. Such compositions are hereby disclosed as if they were expressly disclosed herein.

In one embodiment, the pharmaceutical compositions described herein provide a dosage form of one or more fumarate esters, or prodrugs thereof, for administration to a subject. In one embodiment, the subject is suffering from or has the symptoms of multiple sclerosis or a neurological disease or disorder. The dosage form can be administered, for example, to a subject, or a subject in need thereof. In one aspect, the subject is a mammal, or a mammal in need thereof. In one aspect, the subject is a human, or human in need thereof. In one aspect, the subject is a human. In one aspect, the subject is a child (~0-9 years old) or an adolescent (~10-17 years old). In one aspect, the subject is from about 0 to about 9 years of age. In another aspect, the subject is from about 10 years to about 17 years of age. In another aspect, the subject is over 17 years of age. In another aspect, the subject is an adult (≥18 years of age).

One or more dosage forms can be administered, for example, 1×, 2×, 3×, 4×, 5×, 6×, or even more times per day. One or more dosage forms can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to, general autoimmune or neurodegenerative disorders.

Another embodiment described herein is a method of treating a subject suffering from or having the symptoms of a general autoimmune or neurodegenerative disorder, including multiple sclerosis, by orally administering one or more fumarate esters to the subject. The one or more fumarate esters may be administered in one or more doses, one or more times per day for a total daily dosage.

In one embodiment, the pharmaceutical composition described herein is administered in multiple doses simultaneously. For example, two or more identical doses are administered at one time. In another embodiment, two or more different doses are administered at one time. Such dual or different simultaneous doses can be used to provide an effective amount of the pharmaceutical composition to a subject in need thereof.

In another embodiment, the pharmaceutical compositions described herein may be used to treat, prevent, retard the progression of, delay the onset, ameliorate, reduce the symptoms of, or prophylaxis of general autoimmune or neurodegenerative disorders. Neurodegenerative disorders, as used herein, include multiple sclerosis (MS), which includes relapsing remitting multiple sclerosis (RRMS), secondary progressive multiple sclerosis (SPMS), primary progressive multiple sclerosis (PPMS), progressive relapsing multiple sclerosis (PRvMS), amyotrophic lateral sclerosis (ALS), psoriasis, psoriatic arthritis, Alzheimer's disease, Parkinson's disease, or any combination thereof.

In one embodiment described herein, other conditions, disorders, or diseases are controlled by administration of fumarate esters. The administration of pharmaceutical compositions comprising fumarate esters, as described herein, may be used for treating, preventing, retarding the progression of, delaying the onset, ameliorating, reducing the symptoms of, or prophylaxis of general autoimmune or neurodegenerative disorders, including but not limited to, acute dermatitis, adrenal leukodystrophy, AGE-induced genome damage, Alexander's disease, alopecia areata (totalis and universalis), Alper's disease, Alzheimer's disease, amyotrophic lateral sclerosis, angina pectoris, arthritis, asthma, autoimmune diseases, balo concentric sclerosis, Behçet's syndrome, bullous pemphigoid, Canavan disease, cardiac insufficiency including left ventricular insufficiency, central nervous system vasculitis, Charcot-Marie-Tooth disease, childhood ataxia with central nervous system hypomyelination, chronic active (lupoid) hepatitis, chronic dermatitis, chronic idiopathic peripheral neuropathy, chronic obstructive pulmonary disease, contact dermatitis, Crohn's disease and cutaneous Crohn's disease, cutaneous lupus, cutaneous sarcoidosis, diabetic retinopathy, fibromyalgia, graft versus host disease, granuloma annulare, granulomas including annulare, Grave's disease, Hashimoto's thyroiditis, hepatitis C viral infection, herpes simplex viral infection, human immunodeficiency viral infection, Huntington's disease, inflammatory bowel disease, irritable bowel disorder, ischemia, juvenile-onset diabetes mellitus, Krabbe disease, lichen planus, macular degeneration, mitochondrial encephalomyopathy, monomelic amyotrophy, multiple sclerosis (MS), myocardial infarction, necrobiosis lipoidica, neurodegeneration with brain iron accumulation, neurodermatitis, neuromyelitis optica, neuropathic pain, neurosarcoidosis, NF-κB mediated diseases, optic neuritis, organ transplantation rejection, paraneoplastic syndromes, Parkinson's disease, Pelizaeus-Merzbacher disease, pemphigus, pernicious anemia, primary lateral sclerosis, progressive supranuclear palsy, psoriasis, psoriatic arthritis, pyoderma gangrenosum, radiation-induced dermatitis, radicular pain, radiculopathic pain, reperfusion injury, retinopathic pigmentosa, rheumatoid arthritis (RA), sarcoidosis, sarcoidosis, Schilder's disease, sciatic pain, sciatica, Sjögren's syndrome, subacute necrotizing myelopathy, such as polyarthritis, Susac's syndrome, systemic lupus erythematosus (SLE), tumors, transverse myelitis, ulcerative colitis, or Zellweger syndrome.

In one embodiment, the pharmaceutical compositions described herein are indicated for the treatment of patients with relapsing forms of multiple sclerosis. Another embodiment described herein is a method for treating a patient with a relapsing form of multiple sclerosis comprising the administration of one or more doses of a fumarate ester as described herein. In one aspect, the fumarate ester is dimethyl fumarate, monomethyl fumarate, a prodrug of monomethyl fumarate, or combinations thereof.

Another embodiment described herein is a pharmaceutical composition comprising an oral delayed-release capsule of dimethyl fumarate that is indicated for the treatment of patients with relapsing forms of multiple sclerosis. Another embodiment described herein is a pharmaceutical composition comprising an oral delayed-release capsule of monomethyl fumarate that is indicated for the treatment of patients with relapsing forms of multiple sclerosis. Another embodiment described herein is a pharmaceutical composition comprising an oral delayed-release capsule of dimethyl fumarate, monomethyl fumarate, or a combination thereof that is indicated for the treatment of patients with relapsing forms of multiple sclerosis. Another embodiment described herein is a pharmaceutical composition comprising an oral delayed-release capsule of a pro-drug of monomethyl fumarate that is indicated for the treatment of patients with relapsing forms of multiple sclerosis.

In one embodiment, the pharmaceutical composition comprises a dose of about 60 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, or about 230 mg of one or more fumarate esters. In one aspect, the fumarate ester is dimethyl fumarate, monomethyl fumarate, a pro-drug of monomethyl fumarate, or a combination thereof.

In another embodiment, the composition comprises a dose of about 60 mg to about 80 mg, about 65 mg to about 85 mg, about 70 mg to about 90 mg, about 75 mg to about 95 mg, about 80 mg to about 100 mg, about 85 mg to about 105 mg, about 90 mg to about 110 mg, about 95 mg to about 115 mg, about 100 mg to about 120 mg, about 105 mg to about 125 mg, about 110 mg to about 130 mg, about 115 mg to about 135 mg, about 120 mg to about 140 mg, about 125 mg to about 145 mg, about 130 mg to about 150 mg, about 135 mg to about 155 mg, about 140 mg to about 160 mg, about 145 mg to about 165 mg, about 150 mg to about 170 mg, about 155 mg to about 175 mg, about 160 mg to about 180 mg, about 165 mg to about 185 mg, about 170 mg to about 190 mg, about 175 mg to about 195 mg, about 180 mg to about 200 mg, about 185 mg to about 205 mg, about 190 mg to about 210 mg, about 195 mg to about 215 mg, about 200 mg to about 220 mg, about 205 mg to about 225 mg, about 210 mg to about 230 mg, about 215 mg to about 235 mg, about 220 mg to about 240 mg, about 225 mg to about 245 mg, about 230 mg to about 250 mg, or about 230 mg to about 250 mg of one or more fumarate esters.

In one embodiment, the foregoing compositions can be administered as dosage forms in various regimens, including one dose per day (QD), two doses per day (BID), three doses per day (TID), or four times per day (QID) to achieve a total daily dosage. In another embodiment, any of the foregoing doses comprise a total daily dosage. In another embodiment, any of the foregoing doses may be administered simultaneously, such as two 75 mg, 85 mg, 95 mg, or two 100 mg fumarate ester dosage forms, to provide 150 mg, 160 mg, 190 mg, or 200 mg fumarate ester for a particular dosing period, typically a 24 hour period, or 1 day.

Without being bound by any theory, it is thought that simultaneously administering two or more dosage forms, such as two 75 mg, 80 mg, 85 mg, 90 mg, 95 mg or 100 mg fumarate ester dosage forms (e.g., total fill weight of about 250 to about 300 mg in a No. 5 oval capsule) provides more rapid gastric emptying and transit to the duodenum as compared to a single larger dosage form, such as a single 200 mg fumarate ester dosage form (e.g., total fill weight of about 500 mg to about 600 mg in a No. 12 oval capsule). This regimen may provide a more rapid $T_{max}$ and also reduce $C_{max}$ because of the lower fumarate ester dose. This regimen may also reduce gastrointestinal side effects.

In another embodiment, one or more dosage forms are administered simultaneously or successively over a finite period (such as 1 hour) to provide a dose comprising about 60 mg to about 120 mg, about 65 mg to about 130 mg, about 70 mg to about 140 mg, about 75 mg to about 150 mg, about 80 mg to about 160 mg, about 85 mg to about 170 mg, about 90 mg to about 180 mg, about 95 mg to about 190 mg, about 100 mg to about 200 mg, about 105 mg to about 210 mg, about 110 mg to about 220 mg, about 115 mg to about 230 mg, about 120 mg to about 240 mg, about 125 mg to about 250 mg, about 130 mg to about 260 mg, about 135 mg to about 270 mg, about 140 mg to about 280 mg, about 145 mg to about 290 mg, about 150 mg to about 300 mg, about 155 mg to about 310 mg, about 160 mg to about 320 mg, about 165 mg to about 330 mg, about 170 mg to about 340 mg, about 175 mg to about 350 mg, about 180 mg to about 360 mg, about 185 mg to about 370 mg, about 190 mg to about 380 mg, about 195 mg to about 390 mg, about 200 mg to about 400 mg, about 205 mg to about 410 mg, about 210 mg to about 420 mg, about 215 mg to about 430 mg, about 220 mg to about 440 mg, about 225 mg to about 450 mg, about 230 mg to about 460 mg, or about 230 mg to about 460 mg of one or more fumarate esters.

In another embodiment, one or more dosage forms are administered simultaneously or successively in a finite period to provide a dose comprising about 60 mg to about 180 mg, about 65 mg to about 195 mg, about 70 mg to about 210 mg, about 75 mg to about 225 mg, about 80 mg to about 240 mg, about 85 mg to about 255 mg, about 90 mg to about 270 mg, about 95 mg to about 285 mg, about 100 mg to about 300 mg, about 105 mg to about 315 mg, about 110 mg to about 330 mg, about 115 mg to about 345 mg, or about 120 mg to about 360 mg of one or more fumarate esters.

In another embodiment, one or more dosage forms are administered simultaneously or successively in a finite period multiple time per day to achieve a daily dosage. In one embodiment, the total daily dosage is about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, or about 460 mg of one or more fumarate esters.

In another embodiment, the daily dosage is about 60 mg to about 240 mg, about 65 mg to about 260 mg, about 70 mg to about 280 mg, about 75 mg to about 300 mg, about 80 mg to about 320 mg, about 85 mg to about 340 mg, about 90 mg to about 360 mg, about 95 mg to about 380 mg, about 100 mg to about 400 mg, about 105 mg to about 420 mg, about 110 mg to about 440 mg, about 115 mg to about 460 mg, or about 120 mg to about 480 mg of one or more fumarate esters.

Another embodiment described herein is a method of treating a subject having relapsing forms of multiple sclerosis with one or more dosage forms having a specific dose of fumarate ester. In one aspect, the subject is orally administered one or more pharmaceutical dosage forms as described herein comprising a dose of about 60 mg to about 90 mg of a fumarate ester comprising dimethyl fumarate, monomethyl fumarate, a prodrug of monomethyl fumarate, or a combination thereof twice per day for about seven days. In one aspect, the subject is orally administered one or more pharmaceutical dosage forms as described herein comprising a dose of about 70 mg to about 95 mg of a fumarate ester comprising dimethyl fumarate, monomethyl fumarate, a prodrug of monomethyl fumarate, or a combination thereof twice per day for about seven days. In one aspect, the subject is orally administered one or more pharmaceutical dosage forms as described herein comprising a dose of about 80 mg to about 100 mg of a fumarate ester comprising dimethyl fumarate, monomethyl fumarate, a prodrug of monomethyl fumarate, or a combination thereof twice per day for about seven days.

Another embodiment described herein is a method of treating a subject having relapsing forms of multiple sclerosis with one or more dosage forms having a specific dose of fumarate ester to achieve a total daily dose. In another aspect, the subject is orally administered one or more pharmaceutical dosage forms as described herein comprising a total dose of about 120 to about 180 mg of a fumarate ester comprising dimethyl fumarate, monomethyl fumarate, a prodrug of monomethyl fumarate, or a combination thereof twice per day. In another aspect, the subject is orally administered one or more pharmaceutical dosage forms as described herein comprising a total dose of about 140 to about 190 mg of a fumarate ester comprising dimethyl fumarate, monomethyl fumarate, a prodrug of monomethyl fumarate, or a combination thereof twice per day. In another aspect, the subject is orally administered one or more pharmaceutical dosage forms as described herein comprising a total dose of about 160 to about 200 mg of a fumarate ester comprising dimethyl fumarate, monomethyl fumarate, a prodrug of monomethyl fumarate, or a combination thereof twice per day. In another aspect, the subject is orally administered two pharmaceutical dosage forms as described herein each comprising a dose of about 80 mg to about 100 mg, comprising a total dosage of about 160 to 200 mg, of a fumarate ester comprising dimethyl fumarate, monomethyl fumarate, a prodrug of monomethyl fumarate, or a combination thereof twice per day.

Another embodiment described herein is a pharmaceutical dosage form comprising a pharmaceutical composition as described herein for administration to a subject having multiple sclerosis, comprising a therapeutically effective amount of one or more fumarate esters, wherein the administration is sufficient to achieve a reduction of about 0.224 annualized relapse rate relative to baseline in the subject. In one aspect, the fumarate ester comprises dimethyl fumarate, monomethyl fumarate, a prodrug of monomethyl fumarate, or a combination thereof. In another aspect, the pharmaceutical composition treats multiple sclerosis without substantially inducing one or more of flushing, abdominal pain, diarrhea, and nausea in the subject. In another aspect, the administration does not require titration of the pharmaceutical composition. In another aspect, the dosage form is stable at 25° C. and 60% relative humidity for at least 1 year or 2 years.

In one embodiment described herein, without being bound to any theory, it is surprising and unexpected that the pharmaceutical compositions described herein comprising liquid dosage forms of fumarate ester provide effective treatment of multiple sclerosis at total daily dosages of about 380 mg fumarate ester to about 400 mg fumarate ester when compared to a total daily dosage of 480 mg dimethyl fumarate administered as TECFIDERA®. In one embodiment, the fumarate ester is dimethyl fumarate. In another embodiment, the fumarate ester is monomethyl fumarate. In another embodiment, the fumarate ester is a pro-drug of monomethyl fumarate. In another embodiment, the fumarate ester is monomethyl fumarate. In another embodiment, the fumarate ester is dimethyl fumarate, monomethyl fumarate, a prodrug of monomethyl fumarate, or a combination thereof.

Another embodiment described herein is a pharmaceutical dosage form that has improved bioavailability as compared to another pharmaceutical product. In one aspect, the pharmaceutical dosage form comprising the pharmaceutical composition described herein has improved bioavailability as compared to 240 mg dimethyl fumarate administered as TECFIDERA®. In one aspect, two pharmaceutical dosage forms, each comprising about 80 mg to about 100 mg of dimethyl fumarate, monomethyl fumarate, or a combination thereof, administered to a subject has equivalent pharmacokinetics as one 240 mg dimethyl fumarate dosage form (e.g., TECFIDERA®).

In one embodiment, the pharmaceutical compositions and dosage forms described herein can be administered without titration of the pharmaceutical composition. In one aspect, the pharmaceutical compositions and dosage forms can be administered without titration and without substantially inducing one or more side effects including, but not limited to flushing, abdominal pain, diarrhea, or nausea.

Prior to beginning treatment with the pharmaceutical compositions and dosage forms described herein, a complete blood cell count (CBC) including lymphocyte count, and serum aminotransferase, alkaline phosphatase, and total bilirubin levels should be obtained from the subject in need of treatment.

Fumarate esters can cause flushing and gastrointestinal (GI) side effects in some subjects. While the side effects generally subside after regular treatment, in one aspect the starting dose is about 80 mg to about 100 mg fumarate ester BID orally for the first 7 days. The dose is increased to the effective dose of about 160 mg to about 200 mg fumarate ester BID (e.g., about 320 mg to about 400 mg fumarate ester per day) afterwards. For those subjects who experience GI or flushing side effects, taking the fumarate ester with food can improve tolerability. In one aspect described herein, fumarate ester is administered after a meal. In another aspect described herein, fumarate ester is administered after a high-fat meal to reduce or ameliorate the one or more symptoms of flushing, abdominal pain, diarrhea, and nausea in the subject. In another aspect, about 325 mg of non-enterically coated aspirin or about 200 mg to 400 mg of other NSAID, including acetominophen, ibuprofen, naproxen, diclofenac, salts thereof, or combinations thereof are administered about 0.5 h prior to administration of the fumarate ester composition or dosage form as described herein.

In one aspect, the administration of about 325 mg of non-enteric coated aspirin 30 minutes prior to fumarate ester dosing can reduce the occurrence and severity of flushing. In another aspect, subjects who experience flushing with gastrointestinal side effects may reduce the dose to about 80 mg to about 100 mg fumarate ester BID temporarily, including all integers and fractions within the specified range. Within a month, the effective dose of about 160 mg to about 200 mg fumarate ester BID should be resumed, including all integers within the specified range.

In another embodiment, a subject administered a fumarate ester pharmaceutical composition described herein may be administered one or more leukotriene receptor antagonists. In one embodiment, a subject administered a fumarate ester pharmaceutical composition as described herein may be administered 10 to 20 mg of montelukast (Singulair) or zafirlukast (Accolate®) in conjunction with the fumarate ester.

Another embodiment described herein is a pharmaceutical dosage form that provides delayed release of one or more fumarate esters. In one aspect, the dosage form comprises a soft capsule encapsulating an immediate releasing fill. In another aspect, the pharmaceutical dosage from comprises a fumarate ester, a mixture of mono- and di-glycerides, polyvinylpyrrolidone, polyoxyl 40 hydrogenated castor oil, and lactic acid encapsulated in an soft capsule shell that is coated with a hydroxypropylmethylcellulose coating, a methacrylic acid and ethyl acrylate copolymer, and a polyvinyl alcohol coating. In another aspect, the pharmaceutical dosage form is stable at pH 1.2 for at least 2 hours in an in vitro 2-stage dissolution experiment comprising a USP Apparatus II (e.g., stationary basket over paddle at 100 rpm in 900 mL of media, 37° C.). In another aspect, the pharmaceutical dosage form begins releasing the fill after about 15 minutes at pH 6.8 in an in vitro 2-stage dissolution experiment comprising a USP Apparatus 2 (e.g., stationary basket over paddle at 100 rpm in 900 mL of media, 37° C.). See USP Reference Standard Method <711> Dissolution, which is incorporated by reference for such teachings. In one aspect, the pharmaceutical dosage form releases about 50% of the fill composition after about 52 minutes at pH 6.8. In one aspect, the pharmaceutical dosage form releases about 50% of the fill composition after about 64 minutes at pH 6.8. In one aspect, the pharmaceutical dosage form releases about 48 mg of the fumarate ester after about 52 minutes at pH 6.8. In one aspect, the pharmaceutical dosage form releases about 100 mg of fumarate ester after about 64 minutes at pH 6.8.

Another embodiment described herein is a pharmaceutical dosage form comprising about 190 mg of dimethyl fumarate, monomethyl fumarate, or a combination thereof in a single phase lipid or lipophilic liquid encapsulated in capsule, where upon administration the dosage from provides one or more of the following pharmacokinetic parameters: (a) a mean plasma monomethyl fumarate $C_{max}$ of about 1860 ng/mL; (b) a mean plasma monomethyl fumarate $T_{max}$ of about 3.82 hr; (c) a mean plasma monomethyl fumarate $AUC_{0 \to \tau}$ of about 3060 hr·ng/mL; (d) a mean plasma monomethyl fumarate $AUC_{0 \to \infty}$ of about 3080 hr·ng/mL; (e) a mean plasma monomethyl fumarate AUC % ex of about 1.0%; (f) a mean plasma monomethyl fumarate $K_{el}$ of about 1.4 $hr^{-1}$; or (g) a mean plasma monomethyl fumarate $t_{1/2}$ of about 0.5 hr.

Another embodiment described herein is a pharmaceutical dosage form comprising about 200 mg of dimethyl fumarate, monomethyl fumarate, or a combination thereof in a single phase lipid or lipophilic liquid encapsulated in capsule, where upon administration the dosage from provides one or more of the following pharmacokinetic parameters: (a) a mean plasma monomethyl fumarate $C_{max}$ of about 2370 ng/mL; (b) a mean plasma monomethyl fumarate $T_{max}$ of about 3.8 hr; (c) a mean plasma monomethyl fumarate $AUC_{0 \to \tau}$ of about 3440 hr·ng/mL; (d) a mean plasma monomethyl fumarate $AUC_{0-\infty}$ of about 3470 hr·ng/mL; (e) a mean plasma monomethyl fumarate AUC % ex of about 0.86%; (f) a mean plasma monomethyl fumarate $K_{el}$ of about 1.4 $hr^{-1}$; or (g) a mean plasma monomethyl fumarate $t_{1/2}$ of about 0.5 hr.

Another aspect is one or more pharmaceutical dosage forms, collectively comprising about 160 mg to about 190 mg of dimethyl fumarate, monomethyl fumarate, or a combination thereof in a single-phase lipid or lipophilic liquid encapsulated in capsule, where upon administration the total dose is bioequivalent to 240 mg of dimethyl fumarate (TECFIDERA®). In one aspect, the pharmaceutical dose comprises one capsule. In another aspect, the pharmaceutical dose comprises more than one capsule.

Pharmacokinetics of fumarate esters, particularly dimethyl fumarate, are described by Sheikh et al., *Clinical Therapeutics* 35(10): 1582-1594 (2013), which is incorporated by reference herein for such teachings. Dimethyl fumarate is not quantifiable in plasma following oral administration. After ingestion, dimethyl fumarate is pre-systemically hydrolyzed by esterases and is converted to the active metabolite, monomethyl fumarate (MMF). All pharmacokinetic analyses related to DMF are performed using plasma MMF concentrations because DMF is converted to MMF and DMF is not quantifiable in systemic circulation. If monomethyl fumarate is orally administered, the MMF concentration can be directly measured in plasma.

Another embodiment described herein is a method for treating or reducing the symptoms of a neurodegenerative disorder, including multiple sclerosis, comprising administering to a subject in need thereof one or more of the dosage forms described herein comprising about 190 mg of dimethyl fumarate, monomethyl fumarate, or a combination thereof, where upon administration the dosage from provides one or more of the following pharmacokinetic parameters: (a) a mean plasma monomethyl fumarate $C_{max}$ of about 1860 ng/mL; (b) a mean plasma monomethyl fumarate $T_{max}$ of about 3.82 hr; (c) a mean plasma monomethyl fumarate $AUC_{0 \to \tau}$ of about 3060 hr·ng/mL; (d) a mean plasma monomethyl fumarate $AUC_{0 \to \infty}$ of about 3080 hr·ng/mL; (e) a mean plasma monomethyl fumarate $AUC_{\% \ ex}$ of about 1.0%; (f) a mean plasma monomethyl fumarate $K_{el}$ of about 1.4 $hr^{-1}$; or (g) a mean plasma monomethyl fumarate $t_{1/2}$ of about 0.5 hr.

Another embodiment described herein is a method for treating or reducing the symptoms of a neurodegenerative disorder, including multiple sclerosis, comprising administering to a subject in need thereof one or more of the dosage forms described herein comprising about 200 mg of dimethyl fumarate, monomethyl fumarate, or a combination thereof, where upon administration the dosage from provides one or more of the following pharmacokinetic parameters: (a) a mean plasma monomethyl fumarate $C_{max}$ of about 2370 ng/mL; (b) a mean plasma monomethyl fumarate $T_{max}$ of about 3.8 hr; (c) a mean plasma monomethyl fumarate $AUC_{0 \to \tau}$ of about 3440 hr·ng/mL; (d) a mean plasma monomethyl fumarate $AUC_{0 \to \infty}$ of about 3470 hr·ng/mL; (e) a mean plasma monomethyl fumarate $AUC_{\% \ ex}$ of about 0.86%; (f) a mean plasma monomethyl fumarate $K_{el}$ of about 1.4 $hr^{-1}$; or (g) a mean plasma monomethyl fumarate $t_{1/2}$ of about 0.5 hr.

Another aspect is a method for treating or reducing the symptoms of a neurodegenerative disorder, including multiple sclerosis, comprising administering to a subject in need thereof one or more of the dosage forms described herein comprising about 160 mg to about 190 mg of dimethyl fumarate, monomethyl fumarate, or a combination thereof, where upon administration the dose is bioequivalent to 240 mg of dimethyl fumarate (TECFIDERA®).

Another embodiment described herein is a method for manufacturing an oral pharmaceutical composition comprising the steps of:
  (a) introducing mono- and di-glycerides into a 200 L mixing vessel, adding polyvinylpyrrolidone, and mixing at 400±200 rpm at 60±5° C. for not less than 30 min until the solution is clear;
  (b) adding polyoxyl 40 hydrogenated castor oil and mixing the solution at 400±200 rpm at 60±5° C. for not less than 30 min until the solution is clear;
  (c) adding lactic acid and mixing at 400±200 rpm at 60±5° C. for not less than 30 min until uniformly blended;
  (d) cooling the solution in 200 L tank to 25±5° C. while mixing at 400±200 rpm (a placebo fill can be removed at this step);
  (e) vacuum transferring the solution to a 500 L vacuum deaerator at 20±5° C. and mixing under vacuum for no less than 5 min;
  (f) introducing solid particles of the fumarate ester API (PSD: 40-150 μm) into the deaerator vessel and homogenizing the suspension for no less than 15 min;
  (g) vacuum transferring the suspension to a 200 L medicine tank and deaerating no less than 30 min at 20±5° C.; and
  (h) homogenizing to form a final suspension at 10-50 rpm.

When the pharmaceutical composition is encapsulated in a soft capsule, the following steps are included:
  (i) preparing a gel mass composition comprising a film-forming, water-soluble polymer, an appropriate plasticizer, and solvent;
  (j) casting the gel mass into films or ribbons using heat-controlled drums or surfaces;
  (k) transferring the homogenized suspension of step (h) to an encapsulation line;
  (l) injecting and encapsulating the transferred homogenized fill solution (k) within the gel mass films or ribbons using rotary dye encapsulation to create a capsule;

(m) drying and finishing the capsules;
(n) optionally, coating capsules with a sub-coating and drying;
(o) optionally, coating capsules with a coating and drying;
(p) optionally, coating capsules with a top coating and drying; and
(q) post processing and packaging.

In one aspect, the coatings of steps (n)-(p) are performed in a coating pan. In another aspect, the subcoating of step (n) comprises hydroxypropylmethylcellulose. In another aspect, the coating of step (o) comprises an enteric coating. In another aspect, the coating of step (o) comprises an enteric coating comprising a methacrylic acid and ethyl acrylate copolymer. In another aspect, the coating of step (o) comprises a polyvinyl alcohol coating.

Another embodiment described herein is a method for treating a neurological disease, neurodegenerative disease, autoimmune disease, or an iatrogenic disease or disorder comprising orally administering one or more doses of one or more fumarate esters described herein to a patient in need thereof, wherein the administration activates or modulates one or more cellular signaling pathways. In one aspect, the cellular signaling pathway comprises the nuclear erythroid-derived 2-like 2 (Nrf2) dependent antioxidant response element (ARE) pathway. Without being bound by any theory, it is believed that at least one aspect of the pharmacological activity of the fumarate esters described herein exert an anti-inflammatory and neuroprotective effect in patients with, for example, multiple sclerosis or psoriasis, by activating the Nrf2 cellular signaling pathway. Although not completely understood, the Nrf2 pathway is involved in the cellular response to oxidative stress, which has been linked to neuronal degeneration in multiple sclerosis and in other neurodegenerative or autoimmune diseases (e.g., HIV), see, e.g., Gao et al., Clin. Pharmacol. 6:19-34 (2014), which is incorporated by reference herein for the teachings thereof.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1

Soft capsules comprising particles of a fumarate ester having particle size distributions of PSD: $d90 \leq 100$ μm were manufactured. The dosage forms comprised 95 mg of fumarate ester and comprised 34% fumarate ester, 48% of a mixture of mono- and di-glycerides (e.g., Capmul® MCM), 3% polyvinylpyrrolidone, 10% polyoxyl 40 hydrogenated castor oil, and 5% lactic acid. See Table 6. The matrix fill was encapsulated in soft gelatin capsules comprising 195 Bloom gelatin using rotary die encapsulation. See Table 7. The dosage form was manufactured as number 5 oval capsules. After manufacturing and drying, the capsules were coated with a hydroxypropylmethylcellulose undercoat and dried. The capsules were then coated with an enteric coating containing methacrylic acid, ethyl acrylate copolymer (e.g., EUDRAGIT® L100-55, Evonik; Acryl-EZE®, Colorcon). See Table 8. A polyvinyl alcohol moisture barrier topcoating was applied to the enterically coated capsules (e.g., Opadry® amb II, Clear, Colorcon). See Table 9.

TABLE 6

Fumarate Ester Compositions

| Component | 95 mg Dose Mass (mg) | 95 mg Dose Mass % | 200 mg Dose Mass (mg) | 200 mg Dose Mass % |
| --- | --- | --- | --- | --- |
| Fumarate Ester | 95 | 34.2 | 200 | 34.2 |
| Capmul MCM | 132.5 | 47.8 | 278.9 | 47.8 |
| Povidone K30 | 8.3 | 3.0 | 17.5 | 3.0 |
| Polyoxyl 40 hydrogenated castor oil | 27.7 | 10.0 | 58.4 | 10.0 |
| Lactic Acid | 13.9 | 5.0 | 29.2 | 5.0 |
| TOTAL | 277.4 | 100.0% | 584 | 100.0% |
| Relational Mases and Ratios | Mass (mg) | Mass % | Mass (mg) | Mass % |
| Vehicle Mass | 182.4 | 66 | 384 | 66 |
| Lipid Mass | 168.5 | 61 | 354.8 | 61 |
| API Mass | 95 | 34 | 200 | 34 |
| Mass Ratio API:Lipid | 0.56 | 0.56 | 0.56 | 0.56 |
| Mass Ratio API:Vehicle | 0.52 | 0.52 | 0.52 | 0.52 |

TABLE 7

Exemplary Soft Capsule Shell Composition

| Component | Mass (g) | Mass Percent (%) |
| --- | --- | --- |
| Gelatin, 195 Bloom | 172.4 | 52.2 |
| Polysorb ® 85/70/00 (D-Sorbitol/sorbitans) | 99.0 | 30.0 |
| Purified water | 58.0 | 17.6 |
| Titanium Dioxide | 0.8 | 0.24 |
| FD&C Blue #1 | 0.2 | 0.06 |
| TOTAL | 330.4 | 100.0% |

TABLE 8

Exemplary Enteric Coating Composition
(Acryl-EZE ®, Colorcon)

| Component | Mass (g) | Mass Percent (%) |
|---|---|---|
| Methacrylic acid, ethyl acrylate copolymer | | |
| Talc | | |
| Triethyl citrate | 1826 | 86.6 |
| Sodium bicarbonate | | |
| Colloidal anhydrous silica | | |
| Sodium lauryl sulfate | | |
| Triethyl citrate* | 233.8 | 11.4 |
| Water† | 8236 | 399.8 |
| TOTAL | 2059.8 | 100.0% |

*Additional triethyl citrate added.
†A majority of the water evaporates during the coating process.

TABLE 9

Moisture Barrier Top Coating Composition
(Opadry ® amb II, Clear; Colorcon)

| Component | Mass (g) | Mass Percent (%) |
|---|---|---|
| Polyvinyl alcohol | | |
| Glyceryl mono-caprylate-caprate | | |
| Sodium lauryl sulfate | 600 | 10.0 |
| Talc | | |
| Titanium Dioxide | | |
| Water* | 5400 | 90.0 |
| TOTAL | 6000 | 100.0% |

*A majority of the water evaporates during the coating process.

Example 2

Soft capsules comprising particles of a fumarate ester can be manufactured with 190 mg doses as was done for the 200 mg dose shown in Table 6, above. The capsules can be prepared and coated as described in Example 1 above. See Tables 6-9, above; and see U.S. Pat. No. 10,098,863, which is incorporated by reference herein for such teachings, including pharmacokinetic data for the fumarate ester dosage forms described therein and herein.

TABLE 10

Fumarate Ester Compositions

| | 190 mg Dose | |
|---|---|---|
| Component | Mass (mg) | Mass % |
| Fumarate Ester | 190 | 34.2 |
| Capmul MCM | 266 | 47.8 |
| Povidone K30 | 16.8 | 3.0 |
| Polyoxyl 40 hydrogenated castor oil | 55.5 | 10.0 |
| Lactic Acid | 28 | 5.0 |
| TOTAL | 556.3 | 100.0% |

TABLE 10-continued

Fumarate Ester Compositions

| Relational Mases and Ratios | Mass (mg) | Mass % |
|---|---|---|
| Vehicle Mass | 366.3 | 66 |
| Lipid Mass | 338.3 | 61 |
| API Mass | 190 | 34 |
| Mass Ratio API:Lipid | 0.56 | 0.56 |
| Mass Ratio API:Vehicle | 0.52 | 0.52 |

Example 3

A randomized, 5-week double-blind study was conducted to compare safety and GI tolerability of oral administration of bioequivalent dose regimens of BAFIERTAM™ (MMF) or TECFIDERA® (DMF) to healthy male and female volunteers. The study was conducted to also compare, in healthy subjects, the GI tolerability of BAFIERTAM™ dosed at 190 mg (as 2×95 mg capsules) twice-daily (BID) and TECFIDERA® at 240 mg (as 2×120 mg capsules) BID. See FIG. 1.

Study Drugs

BAFIERTAM™ is a formulation of MMF, the active metabolite of DMF. Monomethyl fumarate is a white to off-white powder. BAFIERTAM™ (MMF) is available as a white, opaque, oval, delayed-release, coated soft gelatin, 95 mg capsule. For the purpose of maintaining the blinding, the storage requirements were matched to that of TECFIDERA®, as BAFIERTAM™ has a shelf life of at least 12 months at 25° C.

TECFIDERA® contains DMF (e.g., dimethyl (E) butene-dioate, ($C_6H_8O_4$)). Dimethyl fumarate is a white to off-white powder that is highly soluble in water. TECFIDERA® is available as hard gelatin delayed-release capsules containing 120 mg of DMF. TECFIDERA® was stored at 15° C. to 30° C. (59 to 86° F.) and was protected from light. Canadian-manufactured TECFIDERA® (Biogen Canada Inc., ON, Canada) was used, which is identical to the US product (Biogen Inc., Cambridge, Mass., USA), except for the manufacturing facility. Both of the study drugs were required to be swallowed whole and intact. Neither were crushed nor chewed, and the capsule contents were not be sprinkled on food. The study drugs may be taken under either fed or fasted conditions.

Study Methodology

Visit 1 of the screening phase (study Days −30 to −1) was completed as an outpatient visit within 30 days prior to Titration. Eligibility to participate based on the inclusion/exclusion criteria was assessed. The screening procedures that were conducted on each potential subject included but were not limited to demographic information, medical and medication histories, physical examinations, clinical laboratory assessments (hematology, biochemistry, serology, urinalysis, urine screening for drugs of abuse and alcohol test), and serum pregnancy test (for female subjects only). All subjects went through a screening phase for up to 30 days, typically 14 days.

Subjects who met all the inclusion and none of the exclusion criteria entered a 5-week Double-Blind Phase. See FIG. 1. The Double-Blind Phase (up to 35 days, study days 1 to 35) occurred in two phases: a Titration Phase that lasted 1 week and a Maintenance Phase that lasted 4 weeks. Visit 2 was Day 1 of the Titration Phase (Days 1 to 7). During Visit 2, subjects enrolled in the study were randomized to either BAFIERTAM™ or TECFIDERA®. The subjects and site staff were blinded to study treatment. Subjects were assigned to treatment based on a gender-stratified randomized scheme generated by PharPoint Research. There were at least 100 subjects per treatment arm randomized 1:1 (BAFIERTAM™: TECFIDERA®) to receive either the study drug BAFIERTAM™ or TECFIDERA® at the Baseline Visit (e.g., after final eligibility for study participation was confirmed). Approximately 50 males and 150 non-pregnant females were randomized to treatment group using a separate randomization schedule for each gender. Female to Male ratio implemented to reflect MS demographics (N=200), though not statistically powered, size informs future study powering should it be pursued based on results. Subjects were instructed to intake one capsule twice daily, approximately 12 hours apart and at approximately the same time of day in the morning and evening. Subjects were instructed to place the capsule in the mouth and not chew them. The capsules were swallowed with as much water as needed. Subjects were advised that the study drug could be taken with or without food.

The subjects were randomly assigned equally into one of the following two treatments by gender: Treatment 1-X and Treatment 2-Y. The double-blind treatment occurred in two phases: a titration phase lasting 1 week and a maintenance phase lasting 4 weeks. Subjects received either BAFIERTAM™ (MMF) delayed-release capsules 95 mg or TECFIDERA® (DMF) delayed-release capsules 120 mg. The study treatments were provided as BAFIERTAM™ and TECFIDERA® capsules that were over-encapsulated to conceal their identity. Blinding was maintained throughout the follow-up period as well. Treatment X was the following: 1×95 mg BAFIERTAM™ (one 95 mg capsule) BID (Banner Life Sciences LLC) during Titration phase; 190 mg BAFIERTAM™ (as two 95 mg capsules) BID (Banner Life Sciences LLC) during Maintenance phase. Treatment Y was the following: 1×120 mg TECFIDERA® (one 120 mg capsule) BID (Biogen Canada Inc., ON, Canada) during Titration phase; 240 mg TECFIDERA® (as two 120 mg capsules) BID (Biogen Canada Inc., ON, Canada) during Maintenance phase.

The first study drug dose of Day 1 was taken in the clinic and all study related procedures and evaluations were performed. The duration of the visit was approximately 7-8 hours but the duration may be extended. Subjects were discharged from the clinic at least 4 hours after the first dose. During the first week of double-blind treatment, study treatment was self-administered as one capsule (with water) BID, approximately every 12 hours (q12h) and at approximately the same time of day, with or without food. For the remaining four weeks of double-blind treatment, study treatment was self-administered as two capsules (with water) BID, approximately every 12 hours (q12h) and at approximately the same time of day, for 4 weeks with or without food. Subjects recorded daily at approximately the same time each morning (24-hour recall) GI symptoms using a provided daily diary, as assessed with the MOGISS. The reporting tool was a mobile application (app) that may be downloaded to a phone/device.

Visit 3 (Day 8 [+1]) was during the Maintenance Phase (Days 8 to 35). Subjects returned to the clinic at the end of the first week of double-blind treatment. During the Maintenance Phase, the subjects were permitted to swallow the capsules sequentially; i.e., one at a time. The duration of the visit was approximately 7-8 hours but may be extended. Subjects were released at minimum 4 hours after dosing. A two-day scheduling window was allowed for the initiation of the Maintenance Phase in case a subject could not come in on Day 8 due to an extenuating circumstance. In that case, the subject came to the clinic on Day 9 for initiation of the Maintenance Phase dosing. A slight overage of medication was provided for the Titration Phase to support this without dose interruption. If this situation occurred, subjects took the Titration dose for an extra day (8 instead of 7 days total) and the first Maintenance dose was taken in the morning of Day 9 in the clinic. The duration of the Maintenance Phase remained the same (28 days), thereby making the total treatment duration 36 days in this case. At the end of each week of maintenance treatment (Day 15±1—Visit 4, Day 22±1—Visit 5, Day 2 9±1—Visit 6), subjects returned to the clinic for an outpatient visit. The visits took approximately 2 hours each. In extenuating circumstances, rescheduling of visits were allowed only within the specified window for each visit.

Visit 7 (Day 36 [+1]) was End-of-Study/Early Termination (End of Maintenance). At the conclusion of the 5th week or in the event of early termination (ET), subjects returned to the center for all End-of-Study (EOS) assessments and procedures. EOS is defined as the date of the last follow-up of the last subject remaining in the study. In extenuating circumstances, the subject came back for EOS procedures on Day 37 instead of Day 36. For subjects who started the Maintenance Phase on Day 9 instead of Day 8, the EOS visit took place on Day 36.

During the Follow-up Phase (2 weeks after EOS) a follow-up phone call occurred within 14 days (+3 d) after the subject completed or discontinued from the study to evaluate the safety of the subject and to collect information on any AEs/serious adverse events (SAEs) that were ongoing at the EOS visit and any new AEs/SAEs that occurred within the 14 days following the EOS/ET. The study subject was asked to return to the site if there were any significant outstanding AEs or SAEs.

Subjects were withdrawn from the study for any of the following: Voluntary withdrawal of consent; The subject was unwilling or unable to comply with the protocol; The subject became pregnant; The subject experienced an AE that necessitated permanent discontinuation of Study Drug; The subject experienced an AE that necessitated unblinding of the Investigator to the subject's treatment assignment; The subject developed clinically significant laboratory test abnormalities; The subject developed clinically significant changes in vital signs; At the discretion of the Investigator for medical reasons; At the discretion of the Investigator or Sponsor for noncompliance; Significant protocol deviation. In the event that subjects were withdrawn or dropped out early for non-medical reasons, e.g., diary-noncompliance, up to 10 additional subjects may be enrolled.

Compliance with treatment dosing was monitored via subject reporting through the daily diary. In addition, subjects were asked to bring their study medication with them to Maintenance Phase and the EOS visits for compliance monitoring. The study medication compliance assessment at the clinic was entered into the eCRF.

Clinical laboratory tests (hematology, serum chemistry, and urinalysis) were repeated prior to discharge at the end of the study or after withdrawal/dismissal of a subject from the study (Table 11). At exit, a full physical exam including vital signs (BP, HR, Temperature, and RR) was conducted upon completion of the study or after withdrawal/dismissal of a subject from the study, where possible.

TABLE 11

| TYPE OF TEST | COMPONENTS | | | |
|---|---|---|---|---|
| Hematology | Hemoglobin Hematocrit | RBC Platelet count | WBC differential Peripheral blood smear | |
| Serum Chemistry | Glucose Calcium Sodium Chloride | Albumin Protein Bilirubin Lactate Dehydrogenase | AST ALT Potassium Alkaline Phosphatase | Urea Uric Acid Creatinine Creatine Kinase |
| Urinalysis | Bilirubin Blood Glucose | pH Ketones Leukocytes | Nitrites Protein | Specific Gravity UBG |
| Additional Tests | Serology (HIV, Hepatitis B surface antigen, Hepatitis C antibody; at screening) | | Breath alcohol test Serum hCG (only females, at Screening) Urine hCG (only females, at each visit check-in) | |
| Urine Tests for Drugs of Abuse | Marijuana, Amphetamines, Phencyclidine, Barbiturates, Cocaine, Opiates, Benzodiazepines | | | |

Presentations by Study Visit

When data were collected serially over time, individual data presentations may include by-study visit displays for all scheduled study visits. Visits were presented according to the nominal visit as obtained from the eCRF (electronic case repor125850t form) or laboratory data unless the visit was an unscheduled visit. Unscheduled visit values were used if the unscheduled visit fell in a visit window and the scheduled visit from the same visit window had a missing value. Visit windows were calculated as shown in Table 12.

TABLE 12

| Study Period | Minimum Study Day | Maximum Study Day |
|---|---|---|
| Screening Week 1 | −30 | −1 |
| Treatment Week 1 | 1 | 7 |
| Treatment Week 2 | 8 | 14 |
| Treatment Week 3 | 15 | 21 |
| Treatment Week 4 | 22 | 28 |
| Treatment Week 5 | 29 | 35 |
| Post-Treatment Week 1 | 36 | 42 |
| Post-Treatment Week 2 | 43 | 49* |

*Follow-up assessment was conducted 14 days (±3 days) after last dose of study medication If multiple clinic visits occurred around the expected date, the clinic visit that occurred closest to the expected date was used for summary presentations. If an assessment was repeated on the expected date, the latest result was used. All assessments were presented in the listings. For the presentation of the MOGISS events, the data was presented according to the study day referred in the diary evaluation; this diary day was noted as Study Day −1.

Terminology

The age of a subject is defined as the number of whole years between the subject's birth date and the date of randomization. If age at randomization was not collected on the CRF (case report form) and only the birth year is known, a birthday of July 1 will be assumed to calculate age at randomization.

Study Drug is the treatment the subject received for the first and subsequent doses. Day 1 (Baseline) is the earliest day that Study Drug is initiated.

Study Day is defined relative to Baseline (Day 1). The Study Day of an event was calculated as: Event Start Date+1—Baseline Date, for dates on or after Day 1; Event Start Date—Baseline Date, for dates before Day 1.

Dairy Day is defined as the Study Day which the diary entry is referring. It was calculated as: Date of Diary Record—1—Baseline Date=Study Day-1.

Baseline Value is defined as the last non-missing value obtained prior to the initiation of Study Drug.

Study Visit is the nominal visit as recorded on the CRF.

Change from Baseline for a given endpoint is defined as the Study Day value minus the Baseline Value.

Last Dose of Study Drug (BAFIERTAM™ or TECFIDERA®) is defined as the last date that the subject received Study Drug as determined by last date of dosing recorded on the eDiary.

Days on Study is defined as the Study Day of the Follow-Up phone contact if the subject has one, otherwise the latest Study Day among the subject's Clinic Visits and eDiary entries.

Duration of Double-Blind Treatment is defined as the number of days from Study Day 1 to the date of Last Dose of Study Drug.

Adherence to Study Drug is defined as the number of capsules administered divided by the number of capsules expected to be administered multiplied by 100. Subjects were expected to take one capsule twice daily from Visit 2 through the day before Visit 3, then two capsules twice daily from Visit 3 through the day before Visit 6. The Study Day of these visits may vary by subject, so the total expected days and total expected dose may also vary per subject. The number of capsules administered were calculated from answers to Daily Diary Questions 1 and 2 (Table 13).

TABLE 13

| Question 1 | Did you take any study medication yesterday? Press 1 for "Yes" Press 2 for "No" |
|---|---|
| Question 2 | If you took both of yesterday's doses press 1 If you took only the morning dose press 2 If you took only the evening dose press 3 |
| Question 3 (Nausea) | Using the touch-tone number on your phone/app, on a scale of zero to 10 with zero being none and 10 being the most extreme please rate the severity of any nausea you have experienced within the last 24 hours. |
| Question 4 (Vomiting) | Using the touch-tone numbers on your phone/app, on a scale of zero to 10 with zero being none and 10 being the most extreme please rate the severity of any vomiting you have experienced within the last 24 hours. |
| Question 5 (Diarrhea) | Using the touch-tone numbers on your phone/app, on a scale of zero to 10 with zero being none and 10 being the most extreme please rate the severity of any diarrhea you have experienced within the last 24 hours. |
| Question 6 (Upper Abdominal Pain) | Using the touch-tone numbers on your phone/app, on a scale of zero to 10 with zero being none and 10 being the most extreme please rate the severity of any UPPER abdominal pain you have experienced within the last 24 hours. |
| Question 7 (Lower Abdominal Pain) | Using the touch-tone numbers on your phone/app, on a scale of zero to 10 with zero being none and 10 being the most extreme please rate the severity of any LOWER abdominal pain you have experienced within the last 24 hours. |
| Question 8 (Constipation) | Using the touch-tone numbers on your phone/app, on a scale of zero to 10 with zero being none and 10 being the most extreme please rate the severity of any constipation you have experienced within the last 24 hours. |
| Question 9 (Bloating) | Using the touch-tone numbers on your phone/app, on a scale of zero to 10 with zero being none and 10 being the most extreme please rate the severity of any bloating you have experienced within the last 24 hours. |

TABLE 13-continued

| | |
|---|---|
| Question 10 (Flatulence) | Using the touch-tone numbers on your phone/app, on a scale of zero to 10 with zero being none and 10 being the most extreme please rate the severity of any flatulence you have experienced within the last 24 hours.<br>Thank you. Your responses have been recorded. |

An adverse event (AE) is any unfavorable and unintended sign, symptom, or disease occurring in any phase of the clinical trial, that may or may not have been considered related to the administration of study drug or to any procedure performed during the study. An AE includes: any abnormal vital sign, 12-lead electrocardiogram (ECG) or clinical laboratory finding that was judged by the Study Investigator to be clinically important, a worsening or exacerbation of a pre-existing symptom or illness, a change in the specificity of a pre-existing condition, and/or an adverse reaction to a concomitant medication. GI AEs were captured on the MOGISS. GI AEs that lead to treatment discontinuation or study withdrawal, or that are classified as serious, were also recorded on CRFs during clinic visits. Non-GI AEs were only recorded on the AE CRF.

All AEs were mapped to a MedDRA preferred term (PT) and SOC (system organ class). All AEs reported were listed for individual subjects showing both verbatim and PTs. A separate listing of serious treatment-emergent AEs was produced. All AEs that occurred prior to the initiation of study treatment or more than 14 days post-study drug discontinuation were excluded from the tables but were included in the listings. All AEs that were reported by subjects providing informed consent but not meeting study entry criteria were listed separately.

Subject incidence rates of all non-GI-AEs were tabulated by MedDRA system organ class, PT, relationship to Study Drug, and severity. If a subject experienced multiple events that map to a single PT, the greatest severity grade and strongest investigator assessment of relation to study medication was assigned to the PT for the appropriate summaries. If an event had a missing severity or relationship, it was classified as having the highest severity and/or strongest relationship to study medication.

Separate summaries of treatment-emergent non-GI-AEs, treatment-emergent SAEs, treatment-emergent AEs potentially related to Study Drug, treatment emergent serious AEs potentially related to Study Drug, and events leading to the withdrawal of Study Drug were generated. Laboratory tests to ensure subject safety including chemistry panel, complete blood count with differential etc., were summarized for each treatment group and gender.

A treatment-emergent adverse event (TEAE) is an AE that occurred during the study (i.e., after the first dose of study drug through 14 days after the last dose of study drug), or that was present prior to dosing and exacerbated during the study. Additionally, it was assumed that an AE which was reported to have started on Day 1 without an associated onset time occurred after the initiation of Study Drug.

A treatment-emergent laboratory toxicity is defined as any post-Baseline laboratory assessment that occurred up to and included 14 days post Study Drug discontinuation representing an increase of 1 grade or more from the Baseline toxicity value. If the Baseline toxicity value was missing, any graded toxicity (grade 1 or higher) that occurred following initiation of Study Drug was considered treatment-emergent.

The MOGISS daily diary was used to assess GI symptoms in the past 24 hours. Currently there is no validated PRO for MS GI evaluation. MOGISS was historically utilized for GI tolerability assessments by BIOGEN in their DMF GI studies NCT01915901 and NCT01568112. The diary consisted of 8 individual symptoms: nausea, vomiting, diarrhea, upper abdominal pain, lower abdominal pain, constipation, bloating, flatulence. Each symptom was graded on an 11-point scale corresponding to a five-category severity index (0=none; 1 to 3=mild; 4 to 6=moderate; 7 to 9=severe; 10=extreme), and was completed each day using 24-hour recall, starting on Study Day 2. The daily diary was administered through an application on the subject's mobile phone or a study-provided device. This did not allow partial completion of the MOGISS; thus 8 symptom scores were present for each time period where the MOGISS was collected.

The MOGISS Composite Symptom Severity Score (MOGISS composite score) is defined as the mean of all 8 individual symptom severity scores within each subject on a given day.

The MOGISS Total Symptom Severity Score (MOGISS total score) is defined as the daily total of all 8 individual daily symptom severity scores within each subject on a given day.

A MOGISS event is defined as one or more consecutive days in which one specific MOGISS symptom has a symptom score 1. Each symptom was counted as a separate event, so a subject may have as many as eight MOGISS events simultaneously. For analyses within a given time interval, the duration and severity are the event's overall duration and highest severity within that treatment period.

The severity of a MOGISS event is the maximum of the symptom score over the duration of the MOGISS event and was classified using the following categories: 0=none; 1 to 3=mild; 4 to 6=moderate; 7 to 9=severe; 10=extreme.

The duration of a MOGISS event is the cumulative number of days on which that MOGISS symptom was reported with a symptom score $\geq 1$.

If a subject experienced more than one MOGISS event of a given type within a treatment period, the Duration of MOGISS Events within that treatment period was defined as the cumulative number of days that at least one event occurred in that period and was the value for the period.

Concomitant medications were those medications taken on or after the initiation of study drug. This definition included medications started prior to the initiation of study drug but continuing concomitantly with study drug.

Prior medications were those medications stopped prior to the initiation of study drug.

Statistical Analysis Plan (SAP)
Multiple Testing and Comparisons

A hierarchical testing strategy was employed by pre-specifying the order in which all primary and secondary endpoints are compared between treatment groups. If there was a statistical difference between treatment groups (p<0.05) in the first primary endpoint, then testing continued to the next primary endpoint until there was not a statistically significant difference between treatment groups (p>0.05), at which point all further tests of the primary endpoint were considered exploratory. If there was a significant difference between treatment groups (p<0.05) in the first primary endpoint, then testing continued to the secondary endpoints and continued until there was not a statistically significant difference between treatment groups (p>0.05), at which point all further tests of the secondary endpoints were considered exploratory. This testing strategy controlled the overall Type-I error rate to 0.05.

Missing Data and Outliers

Missing data may cause biased estimates of treatment effect and change over time. Summary statistics of an individual's raw data were an approach used to simplify analysis of longitudinal data by reducing an individual's data to a single value such as Area Under the Curve (AUC). In situations where it was not possible to obtain all data, parameter estimates from a repeated measures multivariate mixed model was used to compute the AUC summary statistics within treatment groups. This approach has been shown to minimize the bias of treatment effect estimation with many types of missing data patterns. Outliers were examined but not adjusted nor excluded.

The AUC is the summary statistic calculated for each treatment group using the data collected over the 5-week treatment period using the parameter estimates of a repeated measures multivariate mixed model. The AUC was calculated using the ESTIMATE statement from PROC MIXED for the corresponding model.

Timing of Analyses

One analysis was completed after the last randomized subject completed the 14-day post-treatment follow-up period or discontinued from the study and the resulting clinical database was cleaned, quality checked, and locked.

Analysis Population

The population for analysis consisted of all randomized subjects who were administered at least one dose of study drug and were defined as the Safety Population. All subject disposition, demographics, and baseline characteristics, as well as analysis of GI tolerability and safety data were based on this population.

Descriptive statistical methods were used to summarize the observed data from this study by treatment group and gender, with statistical testing performed for the primary and secondary endpoints. Unless stated otherwise, the term "descriptive statistics" refers to number of subjects (n), mean, median, standard deviation (SD), minimum, and maximum for continuous data and frequencies and percentages for categorical data. Significance tests were two-sided and made at the 0.05 level. The statistical analyses were conducted with the SAS System version 9.4 or higher.

Subject Disposition, Demographics and Baseline Characteristics and Medical History Subject disposition, demographics, and baseline characteristics were presented for all randomized and treated subjects by treatment group and gender. The number of randomized subjects, as well as the number of randomized and treated subjects were summarized by treatment group and gender. The number of randomized and treated subjects who completed the study treatment period, completed the study follow-up period, discontinued from the overall study were summarized by treatment group and gender. The reasons for discontinuation of study participation at any time point was also presented by treatment group and gender. Additionally, the number of days on study was summarized by treatment group and gender. Demographic data and baseline characteristics including age, gender, race, ethnicity, height, weight, BMI, and medical history were summarized using descriptive statistics for each double-blind treatment group for the safety population.

GI Tolerability Analysis

The MOGISS was used to assess the global GI events in the past 24 hours (defined as one or more of the following symptoms: nausea, vomiting, diarrhea, upper abdominal pain, lower abdominal pain, constipation, bloating, and flatulence). A subject was counted as having a GI event if he or she had a score of at least 1 for at least one of the GI events. Items were rated on an 11-point numerical scale, where 0=no events; 1 to 3=mild events; 4 to 6=moderate events; 7 to 9=severe events; and 10=extreme events. The MOGISS was completed each day of treatment starting on Day 2 of treatment. Subgroup analyses comparing treatment groups within each gender may be completed for the primary endpoint and key secondary endpoints if warranted. Event duration is defined as the number of consecutive days that each event was reported when the MOGISS was completed. For subjects with more than one GI event during a weekly interval, the event with the highest severity score was used to calculate the frequency of event severity (mild, moderate, severe, extreme), as well as the treatment group mean severity score for each GI event during the assessment interval.

Primary Endpoints

The primary endpoint was the Area Under the Curve (AUC) in each of the individual symptoms over the 5-week treatment period. The symptoms measured were nausea, vomiting, diarrhea, upper abdominal pain, lower abdominal pain, constipation, bloating, and flatulence. The 'Upper Abdominal Pain' and 'Lower Abdominal Pain' scores were averaged for the presentation of 'Abdominal Pain.' The individual symptom scores as defined below were summarized by study day and treatment group. For abdominal pain, summaries for upper and lower abdominal pain were presented in addition to the summary of the average of the two values. For each individual symptom summarized, a repeated measures mixed model with fixed effects for treatment group, gender, study day, treatment group by study day interaction and a random effect for subject was implemented. Least Square Mean Estimates of the daily scores for each treatment were summarized. An AUC for each treatment group was calculated as a linear combination of these values. Differences in the AUC values for each treatment group were assessed using the test statistic from the ESTIMATE statement.

In order to maintain the overall type 1 error rate of 0.05, treatment group comparisons of the individual symptoms were assessed using a hierarchical testing strategy in the following order: (1) Abdominal pain (defined as the within subject daily average of upper abdominal pain and lower abdominal pain); (2) Vomiting; (3) Diarrhea; (4) Nausea; (5) Flatulence; (6) Bloating; (7) Constipation. If there was a statistical difference between treatment groups (p<0.05) then testing was continued to the next symptom until there was not a statistically significant difference between treatment groups (p>0.05), at which point all further tests of the primary endpoint were considered exploratory. The upper abdominal pain and lower abdominal pain individual values were not considered in the hierarchy.

Secondary Endpoints

Secondary endpoints were assessed using a hierarchical testing strategy in the following order: 1) The AUC over the 5-week treatment period in the MOGISS composite score (defined as the daily mean of all 8 individual symptom scores within each subject); 2) Duration of GI events during weeks 1 to 5 of treatment (combined), as assessed by the MOGISS [(Time Frame: Day 1 of treatment to end of treatment (Week 5)]; 3) The AUC over the 5-week treatment period in the MOGISS total score; 4) Number and percentage of subjects reporting GI events during the overall treatment period, as assessed by the MOGISS [Time Frame: Day 1 of treatment to end of treatment (Week 5)]; 5) Worst severity scores of GI events during weeks 1 to 5 of treatment (combined), as assessed by the MOGISS [Time Frame: Day 1 of treatment to end of treatment (Week 5)]; 6) Number and percentage of subjects discontinuing study treatment due to treatment-emergent adverse events [Time Frame: Day 1 of treatment to end of Week 5]; 7) Number and percentage of subjects discontinuing study treatment due to treatment-emergent GI adverse events [Time Frame: Day 1 of treatment to end of Week 5]; 8) Number and percentage of subjects reporting treatment-emergent non-GI adverse events [Time Frame: Day 1 of treatment to end of Week 7]; 9) Number and percentage of subjects reporting serious adverse events [Time Frame: Day 1 of treatment to end of Week 7].

The MOGISS composite scores were summarized by study day and treatment group. A repeated measures mixed model with fixed effects for treatment group, gender, study day, treatment group by study day interaction and a random effect for subject was implemented. An AUC for each treatment group was calculated as a linear combination of the parameter estimates. Differences in the AUC values for each treatment group were assessed using the test statistic from the ESTIMATE statement.

The duration of a MOGISS event during treatment was summarized by treatment group, for each MOGISS symptom and overall MOGISS symptoms for each week of treatment and for the overall treatment period. A MOGISS event present on the subject's last date of treatment or last MOGISS report was considered to end on that date. The treatments were compared by van Elteren test stratified by gender within each time period. This analysis was presented for the total population and by gender. For by-gender analyses, a Wilcoxon Rank Sum test was utilized. The MOGISS total score was analyzed using a repeated measures mixed model in the same manner as defined above for the MOGISS composite score. As an exploratory evaluation of the data, the duration evaluation was repeated for each MOGISS symptom as well as overall MOGISS symptom using scores greater than or equal to 4 (equivalent to Moderate or greater severity per the scale definition).

The number and percentage of subjects reporting MOGISS symptoms during treatment were summarized by treatment group, for each MOGISS symptom as well as overall MOGISS symptoms (using total score 1), for each week of treatment and for the overall treatment period. A Fisher's Exact Test stratified by gender assessed the difference at the two-sided 0.05 significance level. An additional presentation by gender was provided. For by-gender analyses, the Fisher's Exact Test was not stratified.

The frequency and percentage of subjects experiencing extreme, severe, moderate, mild, or no MOGISS symptoms during treatment were summarized by treatment group, by week of treatment and for the overall treatment period, for each MOGISS symptom and overall MOGISS symptoms. For each subject, the corresponding symptom with the maximum symptom score in the time period was summarized by presenting the number and percentage of subjects in each group. The treatments were compared by a Cochran-Mantel-Haenszel (CMH) general association test stratified by gender within each time period. For by-gender analyses, the unstratified CMH test was utilized. An additional analysis of the maximum symptom score treating the severity score as an ordinal value was conducted using a van Elteren test stratified by gender. For the by-gender analyses, the Wilcoxon Rank Sum test was utilized. The analysis was performed separately first including subjects with maximum severity scores of 0 and then repeated excluding subjects with maximum severity of 0.

Discontinuation of Study Treatment

The number and percentage of subjects discontinuing study drug were summarized by treatment group and gender. A Fisher's Exact Test stratified by gender assessed the difference at the two-sided 0.05 significance level. An additional presentation by gender was provided. For by-gender analyses, the Fisher's Exact Test was not stratified.

Clinical Laboratory Assessments

Quantitative laboratory assessments and their corresponding change from baseline values were summarized by visit for each treatment group and gender. Laboratory abnormalities were graded according to the DAIDS Table for Grading Adverse Events for Adults and Pediatrics (version 2.1, July 2017). The number and percentage of subjects experiencing events were summarized by treatment group and gender. Additionally, laboratory results were categorized as low, normal, or high according to laboratory range specifications and the number and percentage of subjects within each category were presented by study visit. Shift from baseline to each scheduled post-baseline was summarized for each normal range category (low, normal, or high) by treatment group and gender. Laboratory values were listed separately for each laboratory panel by subject, laboratory parameter, and date. Laboratory abnormalities that occurred before the initiation of study treatment or more than 14 days post-study drug discontinuation were excluded from the tables but were included in the listings.

Breath Alcohol, ECG, Vital Signs, Physical Examination

Breath alcohol results at each visit were listed. Screening ECG measures were summarized by treatment group and gender. Additionally, these data were listed. Vital signs were presented by visit and treatment group and gender, including change from Baseline. In addition, for Day 1 (baseline pre-dose) and Day 8 vital signs, change from pre-dose were presented. Physical examination results were provided in a listing.

Concomitant Medications

Prior and concomitant medications were coded using the World Health Organization (WHO) Drug Dictionary Enhanced version March 2019. Concomitant medications were summarized for each treatment group and gender by drug classification and generic name, including those that started prior to treatment; prior and concomitant medications were listed.

Protocol Deviations

Deviations from the protocol were assessed by the medical monitoring group and classified as critical, major, or minor. Critical and major protocol deviations were listed.

TABLE 14

| Assessment | S | Week1 Days | | | | | | | | Week 2 Days | | | | | | | Week 3 Days | | | | | | |
|---|---|---|---|---|---|---|---|---|---|---|---|---|---|---|---|---|---|---|---|---|---|---|---|
| | | 1 | 2 | 3 | 4 | 5 | 6 | 7 | $8^a$ | 9 | 10 | 11 | 12 | 13 | 14 | $15^b$ | 16 | 17 | 18 | 19 | 20 | 21 |
| Informed Consent | X | | | | | | | | | | | | | | | | | | | | | |
| Demographics | X | | | | | | | | | | | | | | | | | | | | | |
| Concomitant Medications | X | X | | | | | | | X | | | | | | | X | | | | | | |
| Medical History | X | | | | | | | | | | | | | | | | | | | | | |
| Physical Exam | X | | | | | | | | | | | | | | | | | | | | | |
| Vital Signs (BP, HR, RR, and temperature) | X | | | | | | | | | | | | | | | | | | | | | |
| Vital Signs (BP & HR) | | $X^c$ | | | | | | | $X^c$ | | | | | | | X | | | | | | |
| Height, Weight, and BMI | X | | | | | | | | | | | | | | | | | | | | | |
| 12-Lead ECG | X | | | | | | | | | | | | | | | | | | | | | |
| HIV, HBsAg, HCV | X | | | | | | | | | | | | | | | | | | | | | |
| Urine Drug Screen | X | X | | | | | | | X | | | | | | | X | | | | | | |
| Breath Alcohol Test | X | X | | | | | | | X | | | | | | | X | | | | | | |
| Pregnancy Test (Females) | $X^d$ | $X^e$ | | | | | | | $X^e$ | | | | | | | $X^e$ | | | | | | |
| Laboratory Testing$^f$ | X | | | | | | | | | | | | | | | | | | | | | |
| Liver markers (AST, ALT, total bilirubin, and alkaline phosphatase)$^g$ | | | | | | | | | X | | | | | | | X | | | | | | |
| Inclusion/Exclusion Assessment | X | | | | | | | | | | | | | | | | | | | | | |
| Study Restrictions Assessment | | X | | | | | | | X | | | | | | | X | | | | | | |
| Outpatient visit | X | X | | | | | | | X | | | | | | | X | | | | | | |
| Dosing: In-Clinic$^{h,i}$ | | X | | | | | | | X | | | | | | | | | | | | | |
| Drug Dispensing for Home Dosing$^i$ | | X | | | | | | | X | | | | | | | | | | | | | |
| Subject Training$^j$ | | X | | | | | | | X | | | | | | | | | | | | | |
| Dosing: Home$^k$ | | $X^l$ | X | X | X | X | X | X | $X^l$ | X | X | X | X | X | X | X | X | X | X | X | X | X |
| eDiary - Drug Compliance$^m$ | | | X | X | X | X | X | X | X | X | X | X | X | X | X | X | X | X | X | X | X | X |
| eDiary - MOGISS$^n$ | | | X | X | X | X | X | X | X | X | X | X | X | X | X | X | X | X | X | X | X | X |
| Study Drug Accountability$^m$ | | | | | | | | | X | | | | | | | X | | | | | | |
| Adverse Event Reporting | | X | | | | | | | X | | | | | | | X | | | | | | |

| Assessment | Week 4 Days | | | | | | | Week 5 Days | | | | | | | EOS$^o$ Days | Follow-up$^p$ Days |
|---|---|---|---|---|---|---|---|---|---|---|---|---|---|---|---|---|
| | $22^b$ | 23 | 24 | 25 | 26 | 27 | 28 | $29^b$ | 30 | 31 | 32 | 33 | 34 | 35 | 36 | 36-49 |
| Informed Consent | | | | | | | | | | | | | | | | |
| Demographics | | | | | | | | | | | | | | | | |
| Concomitant Medications | X | | | | | | | X | | | | | | | X | |
| Medical History | | | | | | | | | | | | | | | $X^q$ | |
| Physical Exam | | | | | | | | | | | | | | | X | |
| Vital Signs (BP, HR, RR, and temperature) | | | | | | | | | | | | | | | X | |
| Vital Signs (BP & HR) | X | | | | | | | X | | | | | | | | |
| Height, Weight, and BMI | | | | | | | | | | | | | | | | |
| 12-Lead ECG | | | | | | | | | | | | | | | | |
| HIV, HBsAg, HCV | | | | | | | | | | | | | | | | |
| Urine Drug Screen | X | | | | | | | X | | | | | | | X | |
| Breath Alcohol Test | X | | | | | | | X | | | | | | | X | |
| Pregnancy Test (Females) | $X^e$ | | | | | | | $X^e$ | | | | | | | $X^e$ | |
| Laboratory Testing$^f$ | | | | | | | | | | | | | | | X | |
| Liver markers (AST, ALT, total bilirubin, and alkaline phosphatase)$^g$ | X | | | | | | | X | | | | | | | | |
| Inclusion/Exclusion Assessment | | | | | | | | | | | | | | | | |
| Study Restrictions Assessment | X | | | | | | | X | | | | | | | X | |
| Outpatient visit | X | | | | | | | X | | | | | | | X | |
| Dosing: In-Clinic | | | | | | | | | | | | | | | | |
| Drug Dispensing for Home Dosing$^i$ | | | | | | | | | | | | | | | | |

TABLE 14-continued

| | | | | | | | | | | | | | | | |
|---|---|---|---|---|---|---|---|---|---|---|---|---|---|---|---|
| Subject Training[j] | | | | | | | | | | | | | | | |
| Dosing: Home[k] | | X | X | X | X | X | X | X | X | X | X | X | X | X | |
| eDiary - Drug Compliance[m] | | X | X | X | X | X | X | X | X | X | X | X | X | X | |
| eDiary - MOGISS[n] | | X | X | X | X | X | X | X | X | X | X | X | X | X | |
| Study Drug Accountability[m] | X | | | | | | | X | | | | | | X | |
| Adverse Event Reporting | X | | | | | | | X | | | | | | X | X |

[a] May be scheduled for Day 9 in extenuating circumstances. Subjects were provided with buffer Titration Phase medication to cover for the extra day.
[b] May be scheduled within ±1 day of the indicated study Day.
[c] Vital signs (BP & HR) were measured at pre-dose (0 h), 2, and 4 h after dosing in-clinic.
[d] Serum hCG.
[e] Urine hCG.
[f] Hematology, serum chemistry, and urinalysis.
[g] A blood sample was taken to perform liver function tests.
[h] Two doses were administered with as much water as needed 12 hours apart. Study drug can be taken with or without food.
[i] Study drug may be dispensed within 48 hours prior to providing it to the subject.
[j] During the study visit, trained subjects on dosing, reporting tool use, etc. On Day 8, reinforce training.
[k] Subjects were asked to dose at home twice daily, approximately 12 hours apart, with as much water as needed. Study drug can be taken with or without food.
[l] The morning dose was administered in clinic, and the evening dose was taken at home.
[m] The eDiary was completed on each day of treatment starting on Day 2 in the morning prior to the daily morning dose.
[n] Subjects were required to bring their study drug with them to the clinic visits for pill counts.
[o] In the event of ET, EOS procedures were performed at that time.
[p] Via telephone on Day 49 (+3).
[q] Focused on changes since Screening.

Example 4

Results from Example 3 are presented in the following Tables. Tables 15-16 provide a summary of moderate to extreme GI events (grade ≥4)GI events during the treatment period (weeks 1-5) as reported by MOGISS.

TABLE 15

| | | Grade ≥ 4 (Moderate to Extreme) | |
|---|---|---|---|
| | | Overall | |
| | | BAFIERTAM ™ (N = 105) | TECFIDERA ® (N = 105) |
| Duration of GI Events | N | 105 | 105 |
| | Mean (SD) | 4 (6.9) | 5 (8.4) |
| | Median | 0 | 1 |
| | Min, Max | 0, 34 | 0, 34 |
| | p-value | 0.07 | |
| Lower Abdominal Pain | N | 105 | 105 |
| | Mean (SD) | 1 (3.8) | 1 (3.3) |
| | Median | 0 | 0 |
| | Min, Max | 0, 21 | 0, 18 |
| | p-value | 0.084 | |
| Upper Abdominal Pain | N | 105 | 105 |
| | Mean (SD) | 1 (3.7) | 1 (3.3) |
| | Median | 0 | 0 |
| | Min, Max | 0, 22 | 0, 18 |
| | p-value | 0.633 | |
| Vomiting | N | 105 | 105 |
| | Mean (SD) | 0 (0.3) | 0 (2.4) |
| | Median | 0 | 0 |
| | Min, Max | 0, 3 | 0, 18 |
| | p-value | 0.196 | |
| Diarrhea | N | 105 | 105 |
| | Mean (SD) | 1 (2.7) | 1 (3.1) |
| | Median | 0 | 0 |
| | Min, Max | 0, 20 | 0, 18 |
| | p-value | 0.036 | |
| Nausea | N | 105 | 105 |
| | Mean (SD) | 1 (2.0) | 1 (3.8) |
| | Median | 0 | 0 |
| | Min, Max | 0, 16 | 0, 24 |
| | p-value | 0.188 | |
| Flatulence | N | 105 | 105 |
| | Mean (SD) | 2 (4.6) | 2 (5.6) |
| | Median | 0 | 0 |

TABLE 15-continued

| | | Grade ≥ 4 (Moderate to Extreme) | |
|---|---|---|---|
| | | Overall | |
| | | BAFIERTAM ™ (N = 105) | TECFIDERA ® (N = 105) |
| | Min, Max | 0, 33 | 0, 33 |
| | p-value | 0.663 | |
| Bloating | N | 105 | 105 |
| | Mean (SD) | 2 (5.6) | 2 (5.8) |
| | Median | 0 | 0 |
| | Min, Max | 0, 33 | 0, 33 |
| | p-value | 0.26 | |
| Constipation | N | 105 | 105 |
| | Mean (SD) | 1 (1.9) | 1 (4.0) |
| | Median | 0 | 0 |
| | Min, Max | 0, 15 | 0, 25 |
| | p-value | 0.504 | |

These results show that BAFIERTAM™ has a better GI safety profile compared to TECFIDERA®. Both the frequency and severity of GI symptoms were greater for subjects on TECFIDERA® as compared to BAFIERTAM™. A summary of the moderate or severe GI Adverse Events is shown in Table 16 and FIGS. 2A and 2B.

TABLE 16

Moderate or Severe Gastrointestinal Adverse Events in Healthy Volunteers (%)

| Week | BAFIERTAM ™ | TECFIDERA ® | p-value* | Relative Risk | Relative Risk Reduction |
|---|---|---|---|---|---|
| Week 1 | 36 | 38 | 0.485 | 94.7 | 5.3 |
| Week 2 | 31 | 39 | 0.537 | 79.5 | 20.5 |
| Week 3 | 21 | 38 | 0.009 | 55.3 | 44.7 |
| Week 4 | 17 | 29 | 0.037 | 58.6 | 41.4 |
| Week 5 | 14 | 27 | 0.042 | 51.9 | 48.1 |

Note:
Relative Risk (RR) is the ratio of incidence with BAFIERTAM™ to incidence with TECFIDERA®; Relative Risk Reduction (RRR) is calculated as 1-Relative Risk. Both RR and RRR are expressed as %.

In the secondary analysis, looking at proportion of patients experiencing at least one episode of specific AE, vomiting and diarrhea were statistically significantly lower in BAFIERTAM™ as compared to TECFIDERA®. Tables 17-26.

TABLE 17

Number (%) of subjects with at least 1 GI Event During Treatment Period

| Event | BAFIER-TAM ™ | TECFI-DERA ® | p-value* | Relative Risk | Relative Risk Reduction |
|---|---|---|---|---|---|
| Vomiting | 11% | 23% | 0.043 | 47.8% | 52.2% |
| Diarrhea | 49% | 63% | 0.039 | 77.8% | 22.2% |
| Upper Abdominal Pain | 52% | 58% | 0.483 | 89.7% | 10.3% |
| Lower Abdominal Pain | 56% | 55% | 0.889 | 101.8% | −1.8% |
| Bloating | 59% | 59% | 0.999 | 100.0% | 0.0% |
| Nausea | 61% | 59% | 0.777 | 103.4% | −3.4% |
| Flatulence | 64% | 63% | 0.887 | 101.6% | −1.6% |
| Constipation | 48% | 55% | 0.333 | 87.3% | 12.7% |
| Any GI Event | 86% | 88% | 0.84 | 97.7% | 2.3% |

Note:
Relative Risk (RR) is the ratio of incidence with BAFIERTAM ™ to incidence with TECFIDERA ®; Relative Risk Reduction (RRR) is calculated as 1-Relative Risk. Both RR and RRR are expressed as %.

TABLE 18

Number (%) of subjects with at least 1 Vomiting Event by Study Week

| | Overall | |
|---|---|---|
| | BAFIERTAM ™ (N = 105) | TECFIDERA ® (N = 105) |
| During Treatment Period | 12/105 (11%) | 24/105 (23%) |
| p-value | 0.043 | |
| During Week 1 | 5/105 (5%) | 8/105 (8%) |
| p-value | 0.57 | |
| Relative Risk | 0.478 | |
| Relative Risk Reduction | 0.522 | |
| During Week 2 | 4/99 (4%) | 10/104 (10%) |
| p-value | 0.166 | |
| Relative Risk | 0.4 | |
| Relative Risk Reduction | 0.6 | |
| During Week 3 | 4/98 (4%) | 10/103 (10%) |
| p-value | 0.166 | |
| Relative Risk | 0.4 | |
| Relative Risk Reduction | 0.6 | |
| During Week 4 | 1/95 (1%) | 8/99 (8%) |
| p-value | 0.035 | |
| Relative Risk | 0.125 | |
| Relative Risk Reduction | 0.875 | |
| During Week 5 | 1/92 (1%) | 4/93 (4%) |
| p-value | 0.369 | |
| Relative Risk | 0.25 | |
| Relative Risk Reduction | 0.75 | |

Note:
Relative Risk (RR) is the ratio of incidence with BAFIERTAM ™ to incidence with TECFIDERA ®; Relative Risk Reduction (RRR) is calculated as 1-Relative Risk.

TABLE 19

Number (%) of subjects with at least 1 Diarrhea Event by Study Week

| | Overall | |
|---|---|---|
| | BAFIERTAM ™ (N = 105) | TECFIDERA ® (N = 105) |
| During Treatment Period | 51/105 (49%) | 66/105 (63%) |
| p-value | 0.039 | |
| During Week 1 | 33/105 (31%) | 37/105 (35%) |
| p-value | 0.563 | |
| Relative Risk | 0.886 | |
| Relative Risk Reduction | 0.114 | |
| During Week 2 | 34/99 (34%) | 46/104 (44%) |
| p-value | 0.196 | |
| Relative Risk | 0.773 | |
| Relative Risk Reduction | 0.227 | |
| During Week 3 | 27/98 (28%) | 38/103 (37%) |
| p-value | 0.177 | |
| Relative Risk | 0.757 | |
| Relative Risk Reduction | 0.243 | |
| During Week 4 | 18/95 (19%) | 25/99 (25%) |
| p-value | 0.388 | |
| Relative Risk | 0.76 | |
| Relative Risk Reduction | 0.24 | |
| During Week 5 | 16/92 (17%) | 18/93 (19%) |
| p-value | 0.85 | |
| Relative Risk | 0.895 | |
| Relative Risk Reduction | 0.105 | |

Note:
Relative Risk (RR) is the ratio of incidence with BAFIERTAM ™ to incidence with TECFIDERA ®; Relative Risk Reduction (RRR) is calculated as 1-Relative Risk.

TABLE 20

Number (%) of subjects with at least 1 Upper Abdominal Pain Event by Study Week

| | Overall | |
|---|---|---|
| | BAFIERTAM ™ (N = 105) | TECFIDERA ® (N = 105) |
| During Treatment Period | 55/105 (52%) | 61/105 (58%) |
| p-value | 0.483 | |
| During Week 1 | 40/105 (38%) | 36/105 (34%) |
| p-value | 0.565 | |
| Relative Risk | 1.118 | |
| Relative Risk Reduction | −0.118 | |
| During Week 2 | 41/99 (41%) | 35/104 (34%) |
| p-value | 0.247 | |
| Relative Risk | 1.206 | |
| Relative Risk Reduction | −0.206 | |
| During Week 3 | 26/98 (27%) | 38/103 (37%) |
| p-value | 0.131 | |
| Relative Risk | 0.730 | |
| Relative Risk Reduction | 0.270 | |
| During Week 4 | 21/95 (22%) | 24/99 (24%) |
| p-value | 0.865 | |
| Relative Risk | 0.917 | |
| Relative Risk Reduction | 0.08 | |

TABLE 20-continued

Number (%) of subjects with at least 1
Upper Abdominal Pain Event by Study Week

| | Overall | |
|---|---|---|
| | BAFIERTAM ™ (N = 105) | TECFIDERA ® (N = 105) |
| During Week 5 | 16/92 (17%) | 25/93 (27%) |
| p-value | 0.157 | |
| Relative Risk | 0.630 | |
| Relative Risk Reduction | 0.370 | |

Note:
Relative Risk (RR) is the ratio of incidence with BAFIERTAM ™ to incidence with TECFIDERA ®; Relative Risk Reduction (RRR) is calculated as 1-Relative Risk.

TABLE 21

Number (%) of subjects with at least 1
Lower Abdominal Pain Event by Study Week

| | Overall | |
|---|---|---|
| | BAFIERTAM ™ (N = 105) | TECFIDERA ® (N = 105) |
| During Treatment Period | 59/105 (56%) | 58/105 (55%) |
| p-value | 0.889 | |
| During Week 1 | 44/105 (42%) | 35/105 (33%) |
| p-value | 0.197 | |
| Relative Risk | 1.273 | |
| Relative Risk Reduction | −0.273 | |
| During Week 2 | 39/99 (39%) | 40/104 (38%) |
| p-value | 0.884 | |
| Relative Risk | 1.026 | |
| Relative Risk Reduction | −0.026 | |
| During Week 3 | 29/98 (30%) | 39/103 (38%) |
| p-value | 0.293 | |
| Relative Risk | 0.789 | |
| Relative Risk Reduction | 0.211 | |
| During Week 4 | 24/95 (25%) | 26/99 (26%) |
| p-value | >0.999 | |
| Relative Risk | 0.962 | |
| Relative Risk Reduction | 0.038 | |
| During Week 5 | 19/92 (21%) | 21/93 (23%) |
| p-value | 0.858 | |
| Relative Risk | 0.913 | |
| Relative Risk Reduction | 0.087 | |

Note:
Relative Risk (RR) is the ratio of incidence with BAFIERTAM ™ to incidence with TECFIDERA ®; Relative Risk Reduction (RRR) is calculated as 1-Relative Risk.

TABLE 22

Number (%) of subjects with at least 1
Bloating Event by Study Week

| | Overall | |
|---|---|---|
| | BAFIERTAM ™ (N = 105) | TECFIDERA ® (N = 105) |
| During Treatment Period | 62/105 (59%) | 62/105 (59%) |
| p-value | >0.999 | |
| During Week 1 | 44/105 (42%) | 36/105 (34%) |
| p-value | 0.245 | |
| Relative Risk | 1.235 | |
| Relative Risk Reduction | −0.235 | |
| During Week 2 | 46/99 (46%) | 43/104 (41%) |
| p-value | 0.47 | |
| Relative Risk | 1.1220 | |
| Relative Risk Reduction | −0.1220 | |
| During Week 3 | 37/98 (38%) | 44/103 (43%) |
| p-value | 0.559 | |
| Relative Risk | 0.884 | |
| Relative Risk Reduction | 0.116 | |
| During Week 4 | 34/95 (36%) | 35/99 (35%) |
| p-value | >0.999 | |
| Relative Risk | 1.029 | |
| Relative Risk Reduction | −0.029 | |
| During Week 5 | 29/92 (32%) | 33/93 (35%) |
| p-value | 0.64 | |
| Relative Risk | 0.914 | |
| Relative Risk Reduction | 0.086 | |

Note:
Relative Risk (RR) is the ratio of incidence with BAFIERTAM ™ to incidence with TECFIDERA ®; Relative Risk Reduction (RRR) is calculated as 1-Relative Risk.

TABLE 23

Number (%) of subjects with at least 1
Nausea Event by Study Week

| | Overall | |
|---|---|---|
| | BAFIERTAM ™ (N = 105) | TECFIDERA ® (N = 105) |
| During Treatment Period | 64/105 (61%) | 62/105 (59%) |
| p-value | 0.777 | |
| During Week 1 | 55/105 (52%) | 43/105 (41%) |
| p-value | 0.1 | |
| Relative Risk | 1.268 | |
| Relative Risk Reduction | −0.268 | |
| During Week 2 | 36/99 (36%) | 42/104 (40%) |
| p-value | 0.663 | |
| Relative Risk | 0.900 | |
| Relative Risk Reduction | 0.100 | |
| During Week 3 | 27/98 (28%) | 37/103 (36%) |
| p-value | 0.282 | |
| Relative Risk | 0.778 | |
| Relative Risk Reduction | 0.222 | |
| During Week 4 | 16/95 (17%) | 24/99 (24%) |
| p-value | 0.282 | |
| Relative Risk | 0.708 | |
| Relative Risk Reduction | 0.292 | |
| During Week 5 | 15/92 (16%) | 24/93 (26%) |
| p-value | 0.146 | |
| Relative Risk | 0.615 | |
| Relative Risk Reduction | 0.385 | |

Note:
Relative Risk (RR) is the ratio of incidence with BAFIERTAM ™ to incidence with TECFIDERA ®; Relative Risk Reduction (RRR) is calculated as 1-Relative Risk.

TABLE 24

Number (%) of subjects with at least 1 Flatulence Event by Study Week

| | Overall | |
|---|---|---|
| | BAFIERTAM ™ (N = 105) | TECFIDERA ® (N = 105) |
| During Treatment Period | 67/105 (64%) | 66/105 (63%) |
| p-value | 0.887 | |
| During Week 1 | 48/105 (46%) | 47/105 (45%) |
| p-value | 0.891 | |
| Relative Risk | 1.0159 | |
| Relative Risk Reduction | −0.0159 | |
| During Week 2 | 49/99 (49%) | 50/104 (48%) |
| p-value | 0.889 | |
| Relative Risk | 1.021 | |
| Relative Risk Reduction | −0.021 | |
| During Week 3 | 44/98 (45%) | 47/103 (46%) |
| p-value | >0.999 | |
| Relative Risk | 0.978 | |
| Relative Risk Reduction | 0.022 | |
| During Week 4 | 37/95 (39%) | 44/99 (44%) |
| p-value | 0.557 | |
| Relative Risk | 0.886 | |
| Relative Risk Reduction | 0.114 | |
| During Week 5 | 28/92 (30%) | 34/93 (37%) |
| p-value | 0.438 | |
| Relative Risk | 0.811 | |
| Relative Risk Reduction | 0.189 | |

Note:
Relative Risk (RR) is the ratio of incidence with BAFIERTAM ™ to incidence with TECFIDERA ®; Relative Risk Reduction (RRR) is calculated as 1-Relative Risk.

TABLE 25

Number (%) of subjects with at least 1 Constipation Event by Study Week

| | Overall | |
|---|---|---|
| | BAFIERTAM ™ (N = 105) | TECFIDERA ® (N = 105) |
| During Treatment Period | 50/105 (48%) | 58/105 (55%) |
| p-value | 0.33 | |
| During Week 1 | 28/105 (27%) | 36/105 (34%) |
| p-value | 0.295 | |
| Relative Risk | 0.794 | |
| Relative Risk Reduction | 0.206 | |
| During Week 2 | 28/99 (28%) | 36/104 (35%) |
| p-value | 0.366 | |
| Relative Risk | 0.800 | |
| Relative Risk Reduction | 0.200 | |
| During Week 3 | 21/98 (21%) | 34/103 (33%) |
| p-value | 0.082 | |
| Relative Risk | 0.636 | |
| Relative Risk Reduction | 0.364 | |
| During Week 4 | 23/95 (24%) | 25/99 (25%) |
| p-value | >0.999 | |
| Relative Risk | 0.960 | |
| Relative Risk Reduction | 0.040 | |
| During Week 5 | 17/92 (18%) | 22/93 (24%) |
| p-value | 0.472 | |
| Relative Risk | 0.750 | |
| Relative Risk Reduction | 0.250 | |

Note:
Relative Risk (RR) is the ratio of incidence with BAFIERTAM ™ to incidence with TECFIDERA ®; Relative Risk Reduction (RRR) is calculated as 1-Relative Risk.

TABLE 26

Number (%) of subjects with at least 1 GI Event by Study Week

| | Overall | |
|---|---|---|
| | BAFIERTAM ™ (N = 105) | TECFIDERA ® (N = 105) |
| During Treatment Period | 90/105 (86%) | 92/105 (88%) |
| p-value | 0.84 | |
| During Week 1 | 83/105 (79%) | 73/105 (70%) |
| p-value | 0.118 | |
| Relative Risk | 1.129 | |
| Relative Risk Reduction | −0.129 | |
| During Week 2 | 72/99 (73%) | 75/104 (72%) |
| p-value | >0.999 | |
| Relative Risk | 1.014 | |
| Relative Risk Reduction | −0.014 | |
| During Week 3 | 60/98 (61%) | 72/103 (70%) |
| p-value | 0.235 | |
| Relative Risk | 0.871 | |
| Relative Risk Reduction | 0.129 | |
| During Week 4 | 50/95 (53%) | 66/99 (67%) |
| p-value | 0.057 | |
| Relative Risk | 0.791 | |
| Relative Risk Reduction | 0.209 | |
| During Week 5 | 43/92 (47%) | 54/93 (58%) |
| p-value | 0.142 | |
| Relative Risk | 0.810 | |
| Relative Risk Reduction | 0.190 | |

Note:
Relative Risk (RR) is the ratio of incidence with BAFIERTAM ™ to incidence with TECFIDERA ®; Relative Risk Reduction (RRR) is calculated as 1-Relative Risk.

Figure 2A:
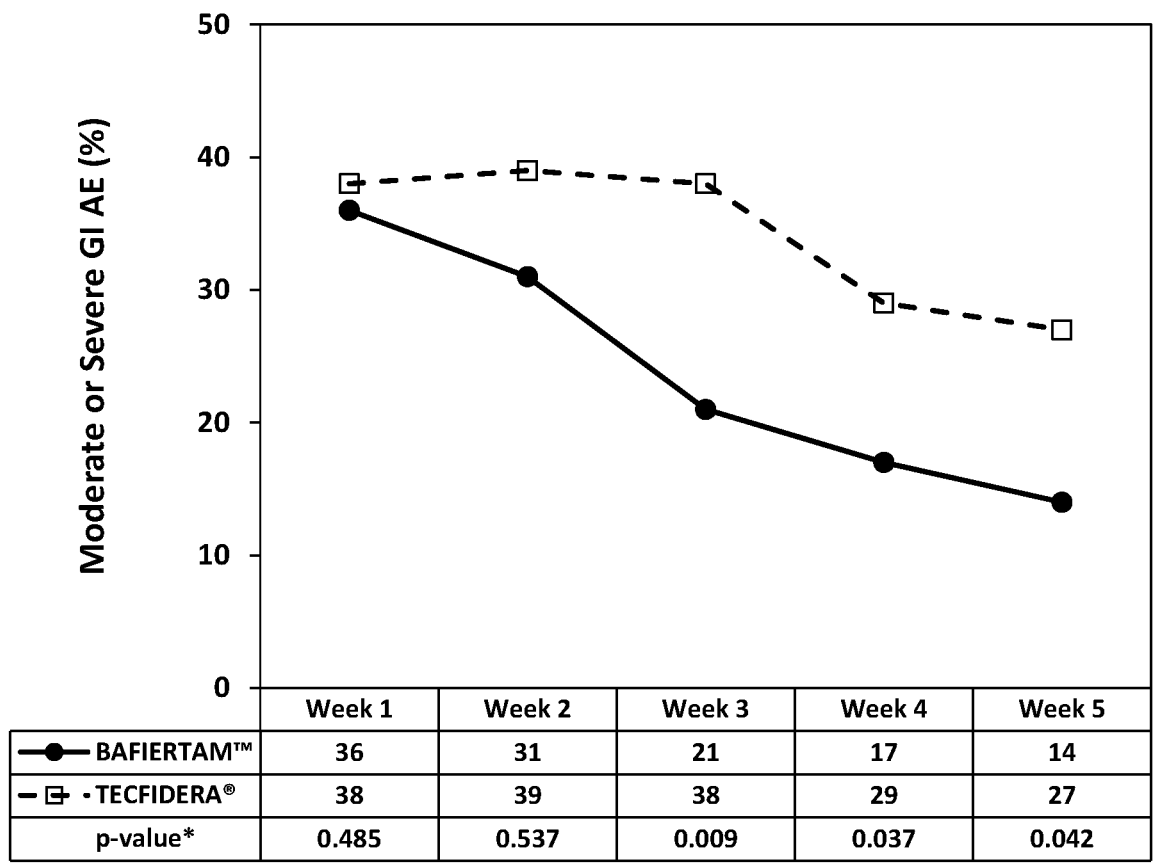
FIG. 2A and FIG. 2B show the percentage of subjects reporting GI adverse events of moderate or greater severity per week.
Figure 2B:
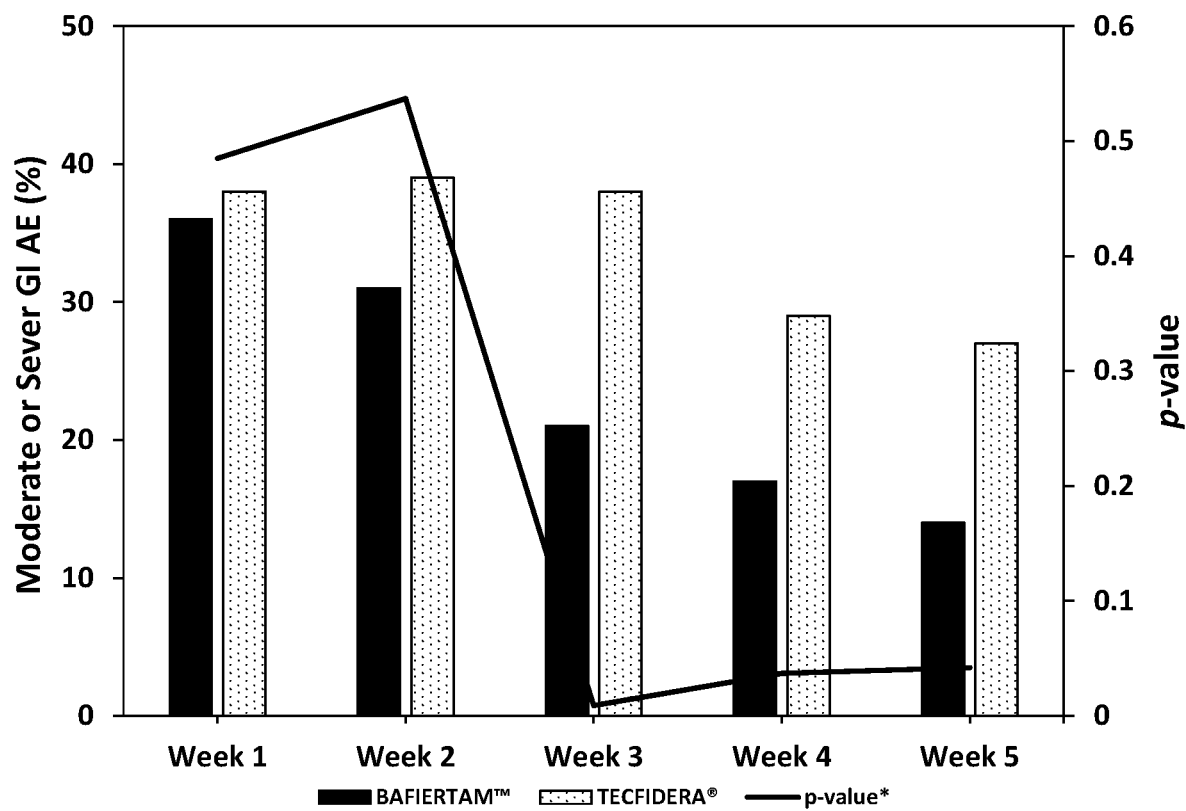

There were no discontinuations due to GI side effects. A significantly faster decline, in the moderate and severe GI symptoms, were observed in the BAFIERTAM™ arm, as compared to the TECFIDERA® arm over the five-week treatment period as illustrated in FIGS. 2A and 2B. The *p-values were calculated for Summary of Duration (Grade ≥4) of GI Events as Reported by MOGISS by Study Week.

In one embodiment, the Relative Risk Reduction (RRR) in the incidence of vomiting and diarrhea is at least 52.2% and 11.4%, respectively, compared with the 120 mg dose of dimethyl fumarate. In another embodiment, the Relative Risk Reduction in the incidence of vomiting is 60-87.5%, and for diarrhea is 10.5-24% compared with the 240 mg dose of dimethyl fumarate. In another embodiment, the Relative Risk Reduction of a gastrointestinal adverse event of at least moderate severity is reduced by between 20.5% and 48.1% compared with the 240 mg dose of dimethyl fumarate. In another aspect, on average the subject experiences a Modified Overall Gastrointestinal Symptom Scale (MOGISS) score of ≤4 for GI events earlier in treatment than would occur in treatment with dimethyl fumarate.

Figure 3:
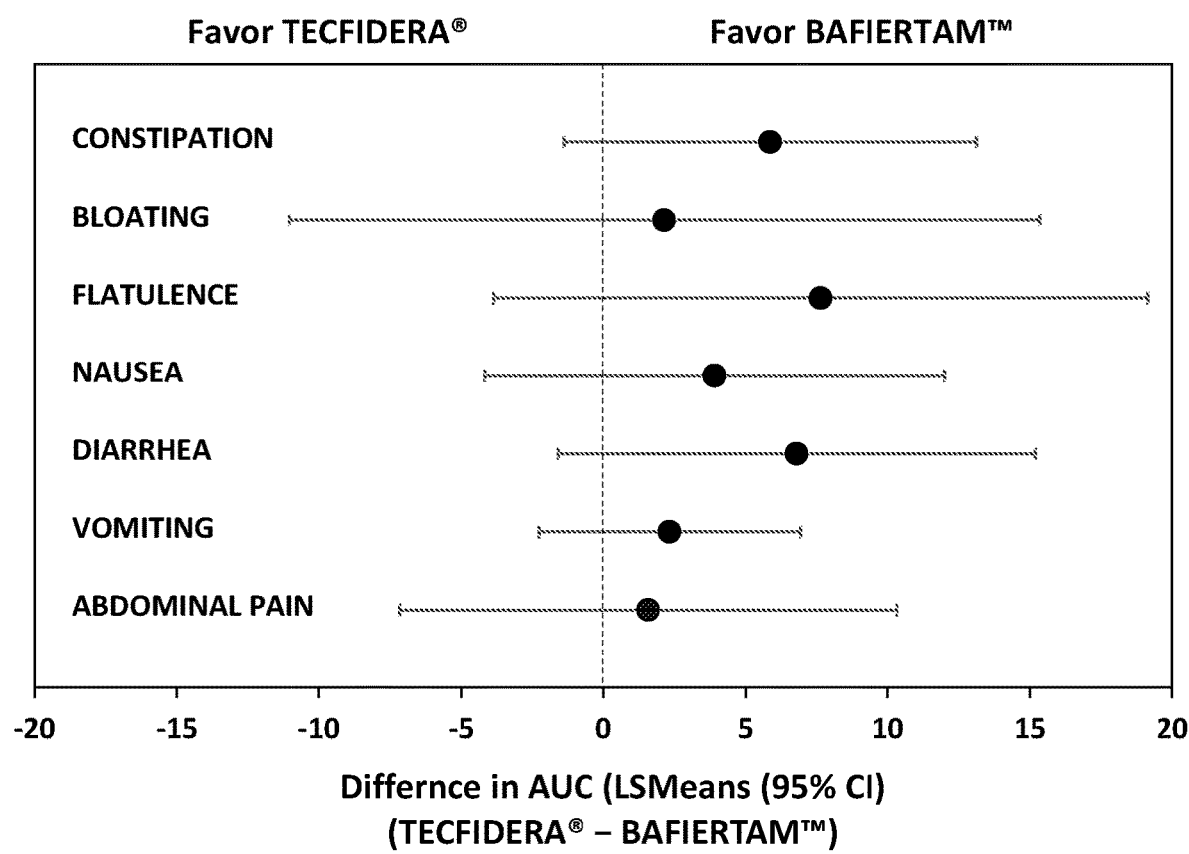
FIG. 3 shows that point estimates for all GI symptoms indicate favoritism for BAFIERTAM™ over TECFIDERA®.
Figure 4:
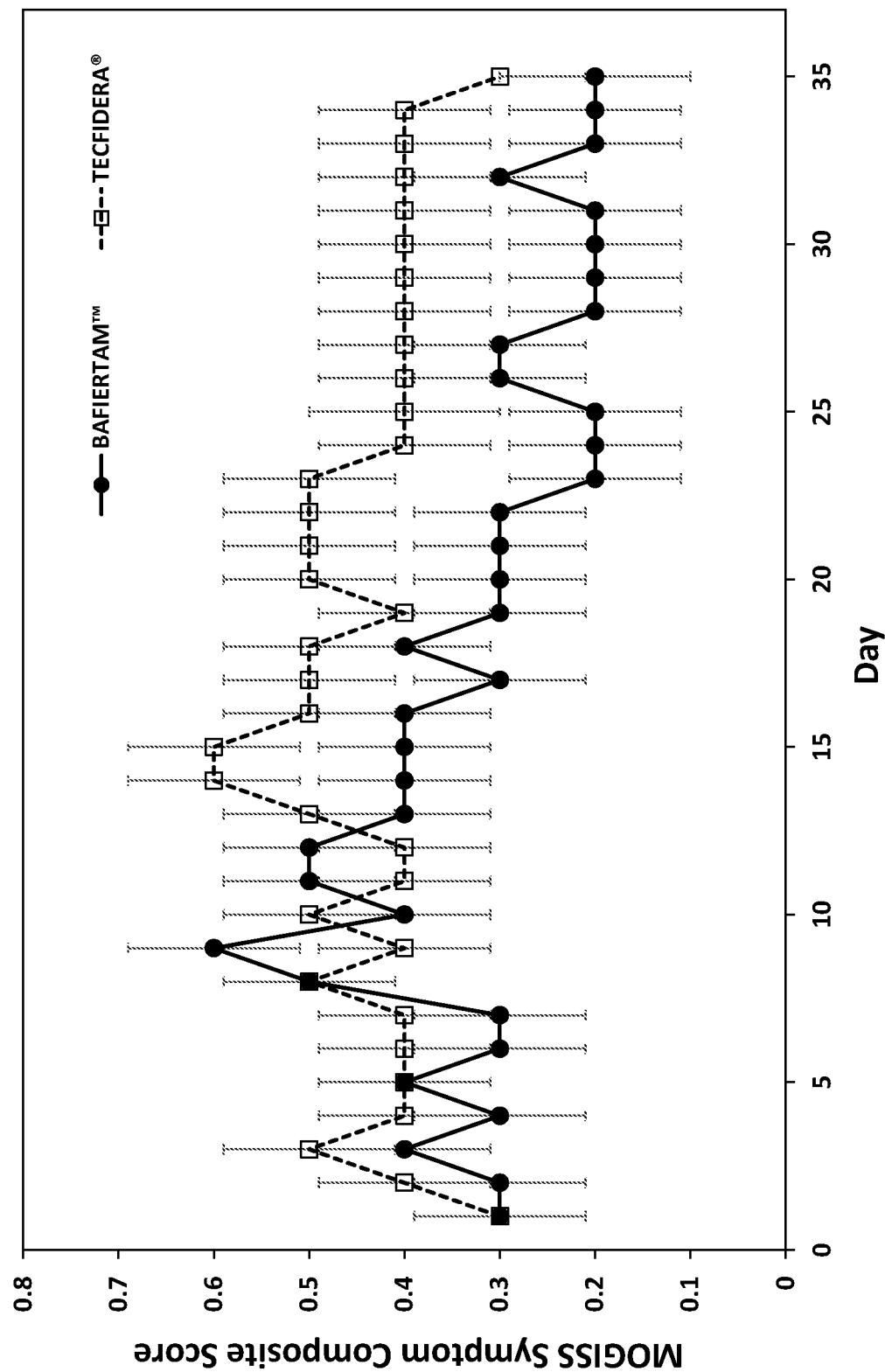
FIG. 4 shows the mean MOGISS Symptom composite score by study date for all subjects.

The point estimates for all GI symptoms favor BAFIERTAM™ over TECFIDERA®, the data presents a consistent trend showing less GI side effects experienced in the BAFIERTAM™ arm as compared to TECFIDERA®. FIG. 2A, 2B, 3.

Collectively, these results suggest that the GI tolerability issues experienced by MS patients administered TECFIDERA® are potentially due to the dimethyl fumarate prodrug. BAFIERTAM™, which has monomethyl fumarate as the active ingredient, has fewer GI adverse events.

The invention claimed is:

1. A method for treating or reducing symptoms of multiple sclerosis or psoriasis in a subject comprising orally administering to a subject in need thereof one or more pharmaceutical dosage forms comprising:
   (a) a single dosage form comprising about 90 mg to about 100 mg of monomethyl fumarate in an immediate releasing single-phase non-aqueous liquid vehicle, wherein administration to the subject provides an effective dosage for the treatment of multiple sclerosis or psoriasis, wherein the incidence of an at least moderate severity gastrointestinal adverse event is at least 5% less frequent and the incidence of vomiting and diarrhea is at least 5% less frequent, as compared to a 120 mg dose of dimethyl fumarate; or
   (b) contemporaneously administering two dosage forms comprising about 85 mg to about 100 mg of monomethyl furmate ot a single dosage form comprising about 170 mg to about 200 mg of monomethyl fumarate in an immediate releasing single-phase non-aqueous liquid vehicle, wherein administration to the subject provides an effective dosage for the treatment of multiple sclerosis or psoriasis, wherein the incidence of an at least moderate severity gastrointestinal adverse event is at least 5% less frequent and the incidence of vomiting and diarrhea is at least 5% less frequent, as compared to a 240 mg dose of dimethyl fumarate; and
   wherein on average the subject experiences a modified Overall Gastrointestinal Symptom Scale (MOGISS) score of ≤4 for GI events earlier in treatment than would occur in treatment with dimethyl fumarate.

2. The method of claim 1, wherein the immediate releasing single-phase nonaqueous liquid vehicle comprises a mixture of mono- and di-glycerides, polyvinylpyrrolidone, polyoxyl 40 hydrogenated castor oil, and lactic acid comprising:
   (a) about 30% to about 35% by mass monomethyl fumarate;
   (b) about 20% to about 50% by mass mono- and di-glycerides;
   (c) about 0.75% to about 5% by mass polyvinyl pyrrolidone;
   (d) about 2% to about 12% by mass polyoxyl 40 hydrogenated castor oil; and
   (e) about 1% to about 5% by mass lactic acid.

3. The method of claim 1, wherein the one or more pharmaceutical dosage forms is encapsulated in an enterically coated soft capsule comprising a shell comprising:
   (a) about 20% to about 36% by weight of at least one film-forming polymer;
   (b) about 8% to about 20% by weight of at least one enteric, acid-insoluble polymer;
   (c) about 15% to about 20% by weight of at least one plasticizer;
   (d) about 1% to about 5% by weight of at least one alkali-neutralizing agent;
   (e) about 20% to about 40% by weight of a solvent;
   (f) about 1% to about 5% by weight of an opacifying agent; and
   (g) about 0.05% to about 1% by weight of at least one coloring agent.

4. The method of claim 1, wherein about 50% of the monomethyl fumarate is released after about 50 min to about 65 min in a pH 6.8 buffer in a USP Apparatus 2 at 37° C.

5. The method of claim 1, wherein the monomethyl fumarate is consistently released to provide a reduction of gastrointestinal side effects.

6. The method of claim 1, wherein the one or more pharmaceutical dosage forms is administered after a meal.

7. The method of claim 6, wherein the meal is a high-fat meal.

8. The method of claim 1, wherein the relative risk reduction (RRR) in the incidence of vomiting and diarrhea is at least 5%, as compared to the 120 mg dose of dimethyl fumarate.

9. The method of claim 8, wherein the RRR in the incidence of vomiting is at least 52.2%, and wherein the RRR in the incidence of diarrhea is at least 11.4%, as compared to the 120 mg dose of dimethyl fumarate.

10. The method of claim 9, wherein the RRR in the incidence of diarrhea is at least about 22.2%, as compared to the 120 mg dose of dimethyl fumarate.

11. The method of claim 1, wherein the relative risk reduction (RRR) in the incidence of vomiting and diarrhea is at least 5%, as compared to the 240 mg dose of dimethyl fumarate.

12. The method of claim 11, wherein the RRR in the incidence of vomiting is about 60-87.5%, and wherein the RRR in the incidence of diarrhea is about 10.5-24%, as compared to the 240 mg dose of dimethyl fumarate.

13. The method of claim 1 wherein the relative risk reduction (RRR) of a gastrointestinal adverse event of at least moderate severity is at least 5%, as compared to the 240 mg dose of dimethyl fumarate.

14. The method of claim 13, wherein the RRR of a gastrointestinal adverse event of at least moderate severity is between about 20.5% and about 48.1%, as compared to the 240 mg dose of dimethyl fumarate.

* * * * *